(12) United States Patent
Yelm et al.

(10) Patent No.: US 8,754,259 B2
(45) Date of Patent: Jun. 17, 2014

(54) SYNTHESIS OF CYCLOHEXANE DERIVATIVES USEFUL AS SENSATES IN CONSUMER PRODUCTS

(71) Applicant: The Proctor & Gamble Company, Cincinnati, OH (US)

(72) Inventors: Kenneth Edward Yelm, Hamilton, OH (US); Gregory Mark Bunke, Lawrenceburg, IN (US); John Christian Haught, West Chester, OH (US)

(73) Assignee: The Proctor & Gamble Company, Cincinnati, OH (US)

( * ) Notice: Subject to any disclaimer, the term of this patent is extended or adjusted under 35 U.S.C. 154(b) by 0 days.

(21) Appl. No.: 13/847,641

(22) Filed: Mar. 20, 2013

(65) Prior Publication Data

US 2013/0216486 A1 Aug. 22, 2013

Related U.S. Application Data

(63) Continuation of application No. 12/541,428, filed on Aug. 14, 2009, now Pat. No. 8,426,643.

(60) Provisional application No. 61/089,094, filed on Aug. 15, 2008.

(51) Int. Cl.
*C07C 231/08* (2006.01)
*C07C 233/58* (2006.01)

(52) U.S. Cl.
USPC .......................... 564/123; 564/158; 564/159

(58) Field of Classification Search
USPC .......................................... 564/123, 189, 190
See application file for complete search history.

(56) References Cited

U.S. PATENT DOCUMENTS

| | | | |
|---|---|---|---|
| 3,111,127 A | 11/1963 | Jarboe | |
| 3,917,613 A | 11/1975 | Humbert et al. | |
| 3,991,178 A | 11/1976 | Humbert et al. | |
| 4,029,759 A | 6/1977 | Humbert et al. | |
| 4,136,163 A | 1/1979 | Watson et al. | |
| 4,150,052 A | 4/1979 | Watson et al. | |
| 4,153,679 A | 5/1979 | Rowsell et al. | |
| 4,157,384 A | 6/1979 | Watson et al. | |
| 4,178,459 A | 12/1979 | Watson et al. | |
| 4,230,688 A | 10/1980 | Rowsell et al. | |
| 4,459,425 A | 7/1984 | Amano et al. | |
| 5,266,592 A | 11/1993 | Grub et al. | |
| 5,451,404 A | 9/1995 | Furman | |
| 5,608,119 A | 3/1997 | Amano et al. | |
| 5,703,123 A | 12/1997 | Pelzer et al. | |
| 5,725,865 A | 3/1998 | Mane et al. | |
| 5,843,466 A | 12/1998 | Mane et al. | |
| 5,977,166 A | 11/1999 | Greenberg | |
| 6,365,215 B1 | 4/2002 | Grainger et al. | |
| 6,451,844 B1 | 9/2002 | Watkins et al. | |
| 6,884,903 B2 | 4/2005 | Lorenz et al. | |
| 6,956,139 B2 | 10/2005 | Green et al. | |
| 7,189,760 B2 | 3/2007 | Erman et al. | |
| 2006/0276667 A1* | 12/2006 | Galopin et al. | ............... 558/410 |
| 2007/0059417 A1 | 3/2007 | Moza et al. | |
| 2010/0040563 A1 | 2/2010 | Haught et al. | |
| 2010/0086498 A1 | 4/2010 | Haught et al. | |
| 2012/0116113 A1* | 5/2012 | Erman et al. | ..................... 560/1 |

FOREIGN PATENT DOCUMENTS

| | | |
|---|---|---|
| EP | 310 299 | 4/1989 |
| GB | 1315626 | 3/1973 |
| WO | WO 02/15692 | 2/2002 |
| WO | WO 2004/037764 | 5/2004 |
| WO | WO 2005/002582 | 1/2005 |
| WO | WO 2005/049553 | 6/2005 |
| WO | WO 2006/103401 | 10/2006 |
| WO | WO 2008/124667 | 10/2008 |

OTHER PUBLICATIONS

Eccles, R. "Menthol and Related Cooling Compounds", J. Pharm. Pharmacol., 46, pp. 618-630, 1994.

Emberger, R. et al., "Synthesis and Sensory Characterization of Menthol Enantiomers and Their Derivatives for the Use in Nature Identical Peppermint Oils," Specialty Chemicals, 7(3), 193-201, 1987.

Givaudan, S.A., "Compounds and Oral Care Compositions in Which They Are Used", Research Disclosure, vol. 522, No. 4, Oct. 1, 2007, p. 983.

Huckel, Walter, "Zur Erkenntnis der Waldenschen Umkehrung", Justus Liebigs Annalen Der Chemie, vol. 533, 1938, pp. 1-45.

Hughes, David L. et al., "The Effect of Acid Strength on the Mitsunobu Esterification Reaction: Carobxyl vs. Hydroxyl Reactivity", Journal of Organic Chemistry, vol. 61, 1996, pp. 2967-2971.

(Continued)

*Primary Examiner* — Shailendra Kumar
(74) *Attorney, Agent, or Firm* — James E. Oehlenschlager

(57) ABSTRACT

The present invention provides synthetic routes for preparing various isomers of cyclohexane-based coolants, such as menthyl esters and menthanecarboxamide derivatives, in particular those substituted at the amide nitrogen, for example with an aromatic ring or aryl moiety. Such structures have high cooling potency and long lasting sensory effect, which make them useful in a wide variety of consumer products. One synthetic route involves a copper catalyzed coupling of a primary menthanecarboxamide with an aryl halide, such reaction working best in the presence of potassium phosphate and water. Using this synthetic route, specific isomers can be prepared including the menthanecarboxamide isomer having the same configuration as l-menthol and new isomers such as a neoisomer having opposite stereochemistry at the carboxamide (C-1) position. The neoisomer unexpectedly has potent and long lasting cooling effect. Preparation schemes for neoisomers of other menthyl derivatives which are useful as coolants, including esters, ethers, carboxy esters and other N-substituted carboxamides are also provided.

7 Claims, No Drawings

(56) References Cited

OTHER PUBLICATIONS

International Search Report for PCT/US2009/053633, 2009.
International Search Report for PCT/US2009/053634, 2009.
Rovner, Sophie L., "Better Than Mint Medicinal Chemistry Methods Lead to New Cooling Compounds that are more potent and last longer than menthol", Chemical & Engineering News, 2007, 85(39), pp. 95-98/.
Watson, H.R. et al., New Compounds With the Menthol Cooling Effect, J. Soc. Cosmet. Chem., 29, pp. 185-200, 29, 1978.
Wei et al., "AG-3-5: a chemical producing sensations of cold", J. Pharm. Pharmacol., 1983, 35:110-112.

* cited by examiner

SYNTHESIS OF CYCLOHEXANE DERIVATIVES USEFUL AS SENSATES IN CONSUMER PRODUCTS

This application is a CON of Ser. No. 12/541,428 Aug. 14, 2009 U.S. Pat. No. 8,426,643 which claims benefit of 61/089,094 Aug. 15, 2008.

TECHNICAL FIELD

The present invention relates to preparation of cyclohexane-based derivatives useful as sensates for consumer products such as oral care and skin care compositions. In one aspect, synthesis pathways are developed for preparing various isomers of cyclohexane-based coolants, such as menthyl esters, menthyl ethers and menthanecarboxamide derivatives, in particular those substituted at the amide nitrogen.

BACKGROUND OF THE INVENTION

Coolants or compounds that have a physiological cooling effect particularly on oral and other mucosal surfaces and skin are common ingredients in a wide variety of consumer products including edible compositions and personal and health care compositions and in flavor or perfume compositions for use in such products. Examples of edible compositions include confectionery, candies, chocolate, chewing gum, beverages and oral medicines. Personal care compositions for application to the skin, hair and mucosal surfaces include lotions or creams, skin cleansers, shampoos and conditioners, wipes and towelettes and cosmetic products such as lipsticks and foundations. A particular class of personal and health care compositions to which the present invention relates is for oral and throat care, which include products in powder, paste or liquid forms and which on being used are retained for a time sufficient to contact the surface and the internal mucous membrane of the oral or nasal cavities or the pharynx. Such products include for example, mouthwashes, dental and throat lozenges, gargles, chewing gum, dentifrice or toothpastes, toothpicks, dental tablets and powders and topical solutions for application in dental treatment, as well as cough-syrups, chewable antacids and digestion promoting preparations.

The pleasant cooling sensation provided by coolants contributes to the appeal and acceptability of the products. In particular, oral care products such as dentifrices and mouthwashes are formulated with coolants because they provide breath freshening effects and a clean, cool, fresh feeling in the mouth.

A large number of coolant compounds of natural or synthetic origin have been described. The most well-known compound is menthol, particularly l-menthol, which is found naturally in peppermint oil, notably of *Mentha arvensis L* and *Mentha viridis L*. Of the isomers of menthol, the l-isomer occurs most widely in nature and is typically what is referred by the name menthol having coolant properties. L-menthol has the characteristic peppermint odor, has a clean fresh taste and exerts a cooling sensation when applied to the skin and mucosal surfaces. Other isomers of menthol (neomenthol, isomenthol and neoisomenthol) have somewhat similar, but not identical odor and taste, i.e., having disagreeable notes described as earthy, camphor, musty. The biggest difference among the isomers is in their cooling potency. L-menthol provides the most potent cooling, i.e., having the lowest cooling threshold of about 800 ppb, i.e., the concentration where the cooling effect could be clearly recognized. At this level, there is no cooling effect for the other isomers. For example, d-neomenthol is reported to have a cooling threshold of about 25,000 ppb and l-neomenthol about 3,000 ppb. [R. Emberger and R. Hopp, "Synthesis and Sensory Characterization of Menthol Enantiomers and Their Derivatives for the Use in Nature Identical Peppermint Oils," *Specialty Chemicals* (1987), 7(3), 193-201]. This study demonstrated the outstanding sensory properties of l-menthol in terms or cooling and freshness and the influence of stereochemistry on the activity of these molecules.

Among synthetic coolants, many are derivatives of or are structurally related to menthol, i.e., containing the cyclohexane moiety, and derivatized with functional groups including carboxamide, ketal, ester, ether and alcohol. Examples include the ρ-menthanecarboxamide compounds such as N-ethyl-ρ-menthan-3-carboxamide, known commercially as "WS-3", and others in the series such as WS-5 (N-ethoxycarbonylmethyl-ρ-menthan-3-carboxamide), WS-12 [N-(4-methoxyphenyl)-ρ-menthan-3-carboxamide] and WS-14 (N-tert-butyl-ρ-menthan-3-carboxamide). Examples of menthane carboxy esters include WS-4 and WS-30. An example of a synthetic carboxamide coolant that is structurally unrelated to menthol is N,2,3-trimethyl-2-isopropylbutanamide, known as "WS-23". Additional examples of synthetic coolants include alcohol derivatives such as 3-(l-menthoxy)-propane-1,2-diol known as TK-10, isopulegol (under the tradename Coolact P) and ρ-menthane-3,8-diol (under the tradename Coolact 38D) all available from Takasago; menthone glycerol acetal known as MGA; menthyl esters such as menthyl acetate, menthyl acetoacetate, menthyl lactate known as Frescolat® supplied by Haarmann and Reimer, and monomenthyl succinate under the tradename Physcool from V. Mane. TK-10 is described in U.S. Pat. No. 4,459,425 to Amano et al. Other alcohol and ether derivatives of menthol are described e.g., in GB 1,315,626 and in U.S. Pat. Nos. 4,029,759; 5,608,119; and 6,956,139. WS-3 and other carboxamide cooling agents are described for example in U.S. Pat. Nos. 4,136,163; 4,150,052; 4,153,679; 4,157,384; 4,178,459 and 4,230,688. Additional N-substituted ρ-menthane carboxamides include amino acid derivatives such as those disclosed in WO 2006/103401 and in U.S. Pat. Nos. 4,136,163; 4,178,459 and 7,189,760 such as N-((5-methyl-2-(1-methylethyl)cyclohexyl)carbonyl)glycine ethyl ester and N-((5-methyl-2-(1-methylethyl)cyclohexyl)carbonyl)alanine ethyl ester. Menthyl esters including those of amino acids such as glycine and alanine are disclosed e.g., in EP 310,299 and in U.S. Pat. Nos. 3,111,127; 3,917,613; 3,991,178; 5,5703,123; 5,725,865; 5,843,466; 6,365,215; 6,451,844; and 6,884,903. Ketal derivatives are described, e.g., in U.S. Pat. Nos. 5,266,592; 5,977,166 and 5,451,404. Additional agents that are structurally unrelated to menthol but have been reported to have a similar physiological cooling effect include alpha-keto enamine derivatives described in U.S. Pat. No. 6,592,884 including 3-methyl-2-(1-pyrrolidinyl)-2-cyclopenten-1-one (3-MPC), 5-methyl-2-(1-pyrrolidinyl)-2-cyclopenten-1-one (5-MPC), and 2,5-dimethyl-4-(1-pyrrolidinyl)-3(2H)-furanone (DMPF); icilin (also known as AG-3-5, chemical name 1-[2-hydroxyphenyl]-4-[2-nitrophenyl]-1,2,3,6-tetrahydropyrimidine-2-one) described in Wei et al., *J. Pharm. Pharmacol.* (1983), 35:110-112. Reviews on the coolant activity of menthol and synthetic coolants include H. R. Watson, et al. *J. Soc. Cosmet. Chem.* (1978), 29, 185-200 and R. Eccles, *J. Pharm. Pharmacol.*, (1994), 46, 618-630.

Many of the compounds above including menthol have relatively low potency and the duration of the cooling effect is typically short-lived. Thus, it is necessary to include fairly high levels of such compounds when formulating products, which increases cost. In addition, many of these compounds are relatively high cost ingredients since they are expensive to manufacture on an industrial scale. Therefore, compounds with high cooling potency and long lasting sensory effect are highly sought that will require only small amounts for incorporation in a variety of consumer products to provide high impact and long-lasting effect. Such potent and long lasting coolant compounds have recently been described for example in WO 2005/049553A1 to Givaudan including ρ-menthane carboxamides substituted at the N-position with an aryl moiety bearing certain substituents. Examples include N-(4-cyanomethylphenyl)-ρ-menthanecarboxamide; N-(4-sulfamoylphenyl)-ρ-menthanecarboxamide; N-(4-cyanophenyl)-ρ-menthanecarboxamide; N-(4-acetylphenyl)-ρ-menthanecarboxamide, N-(4-hydroxymethylphenyl)-ρ-menthanecarboxamide and N-(3-hydroxy-4-methoxyphenyl)-ρ-menthanecarboxamide. In particular, an isomer having the same configuration as l-menthol, i.e., N-[4-(cyanomethyl)phenyl]-(1R,2S,5R)-2-isopropyl-5-methylcyclohexanecarboxamide, has been commercialized by Givaudan under the trade name Evercool 180 (also referred to as G-180), supplied as a solution in a flavor oil such as spearmint or peppermint [*Chemical & Engineering News* (2007), 85(39), pp. 95-98]. This material has been demonstrated to provide intense and long-lasting cooling effect and useful for incorporation in personal care products such as dentifrice and mouthwash as described in commonly assigned U.S. Application No. 61/003,863, filed Nov. 20, 2007.

Similar to other commercially available synthetic coolants, the new Givaudan Evercool (G-180) coolant is a relatively expensive ingredient. It is believed that this is due to the high cost of producing, purifying and solubilizing the material. Givaudan's proposed synthetic route for the Evercool material as described in WO 2005/049553A1 involves reacting a menthane acid chloride with an aminobenzyl cyanide, the latter believed to be a relatively expensive raw material. Thus in one aspect, the present invention provides an alternate synthesis pathway for preparing menthane carboxamide derivatives utilizing significantly less expensive raw materials while achieving good yield. Additionally, methods of purifying and solubilizing coolant compounds are provided which facilitate incorporation of the coolants into a wide variety of consumer products.

SUMMARY OF THE INVENTION

The present invention provides synthetic routes for preparing various isomers of cyclohexane-based coolants, such as menthyl esters and menthanecarboxamide derivatives, in particular those substituted at the amide nitrogen, for example with an aromatic ring or aryl moiety. Such structures have high cooling potency and long lasting sensory effect, which make them useful in a wide variety of consumer products. One synthetic route involves a copper catalyzed coupling of a primary menthanecarboxamide with an aryl halide, such reaction working best in the presence of potassium phosphate and water. Using this synthetic route, specific isomers can be prepared including the menthanecarboxamide isomer having the same configuration as l-menthol and new isomers such as a neoisomer having opposite stereochemistry at the carboxamide (C-1) position. The neoisomer unexpectedly has potent and long lasting cooling effect. Neoisomers of other derivatives including menthyl esters, menthyl ethers, menthanecarboxy esters and other N-substituted menthanecarboxamides are also prepared and demonstrated to be useful as coolants.

DETAILED DESCRIPTION OF THE INVENTION

While the specification concludes with claims particularly pointing out and distinctly claiming the invention, it is believed that the present invention will be better understood from the following description.

All percentages and ratios used hereinafter are by weight of total composition, unless otherwise indicated. All percentages, ratios, and levels of ingredients referred to herein are based on the actual amount of the ingredient, and do not include solvents, fillers, or other materials with which the ingredient may be combined as a commercially available product, unless otherwise indicated.

All measurements referred to herein are made at 25° C. unless otherwise specified.

Herein, "comprising" means that other steps and other components which do not affect the end result can be added. This term encompasses the terms "consisting of" and "consisting essentially of."

As used herein, the word "include," and its variants, are intended to be non-limiting, such that recitation of items in a list is not to the exclusion of other like items that may also be useful in the materials, compositions, devices, and methods of this invention.

As used herein, the words "preferred", "preferably" and variants refer to embodiments of the invention that afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the invention.

By "oral care composition" is meant a product, which in the ordinary course of usage, is not intentionally swallowed for purposes of systemic administration of particular therapeutic agents, but is rather retained in the oral cavity for a time sufficient to contact substantially all of the dental surfaces and/or oral tissues for purposes of oral activity. The oral care composition may be in various forms including toothpaste, dentifrice, tooth gel, subgingival gel, mouthrinse, mousse, foam, mouthspray, lozenge, chewable tablet, chewing gum or denture product. The oral care composition may also be incorporated onto strips or films for direct application or attachment to oral surfaces.

The term "dentifrice", as used herein, includes paste, gel, or liquid formulations unless otherwise specified. The dentifrice composition may be a single phase composition or may be a combination of two or more separate dentifrice compositions. The dentifrice composition may be in any desired form, such as deep striped, surface striped, multilayered, having a gel surrounding a paste, or any combination thereof. Each dentifrice composition in a dentifrice comprising two or more separate dentifrice compositions may be contained in a physically separated compartment of a dispenser and dispensed side-by-side.

The term "dispenser", as used herein, means any pump, tube, or container suitable for dispensing compositions such as dentifrices.

The term "teeth", as used herein, refers to natural teeth as well as artificial teeth or dental prosthesis.

The term "orally acceptable carrier or excipients" includes safe and effective materials and conventional additives such as used in oral care compositions including but not limited to fluoride ion sources, anti-calculus or anti-tartar agents, buffers, abrasives such as silica, alkali metal bicarbonate salts, thickening materials, humectants, water, surfactants, titanium dioxide, flavorants, sweetening agents, xylitol, coloring agents, and mixtures thereof.

Active and other ingredients useful herein may be categorized or described herein by their cosmetic and/or therapeutic benefit or their postulated mode of action or function. However, it is to be understood that the active and other ingredients useful herein can, in some instances, provide more than one cosmetic and/or therapeutic benefit or function or operate via more than one mode of action. Therefore, classifications herein are made for the sake of convenience and are not intended to limit an ingredient to the particularly stated function(s) or activities listed.

Herein, the terms "tartar" and "calculus" are used interchangeably and refer to mineralized dental plaque biofilms.

In one aspect, the present invention provides a synthesis pathway for preparing various isomers of cyclohexane-based carboxamide coolants, such as those substituted at the carboxamide N-position. Preferred substituents include an aryl moiety, such as a phenyl ring which may also bear particular substituents. One pathway involves a copper catalyzed coupling of a primary carboxamide with an aryl halide such as illustrated below. In addition to the copper catalyst, a key driver to this coupling reaction is the presence of potassium phosphate. The addition of water to the reaction medium produces consistent results. The copper catalyst may be provided for example by a copper halide such as copper (I) iodide. This reaction is a modification of a related procedure described in *Journal of the American Chemical Society* (2002), 124(25), 7421-7428.

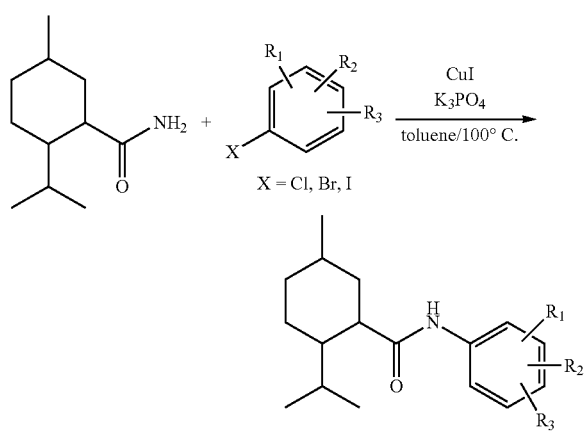

In the above structures $R_1$, $R_2$ and $R_3$ may be the same or different and may each be hydrogen or one of $R_1$, $R_2$ and $R_3$ may be a group selected from halogen, OH, hydroxy-C1-C4-alkyl, C1-C4-alkoxy, $NO_2$, CN, cyano-C1-C4-alkyl, acetyl, $SO_2NH_2$, CHO, $CO_2H$ and C1-C4 alkyl carboxylate; two of $R_1$, $R_2$ and $R_3$ may be H or C1-C4 alkyl. Preferably $R_1$ is a group selected from CN, cyanomethyl, acetyl, $SO_2NH_2$, hydroxymethyl and $OCH_3$ at the 4-position and both $R_2$ and $R_3$ are H.

Specifically, this chemistry can be applied to produce the coolant G-180, chemically N-[4-(cyanomethyl)phenyl]-(1R, 2S,5R)-2-isopropyl-5-methylcyclohexanecarboxamide, as follows:

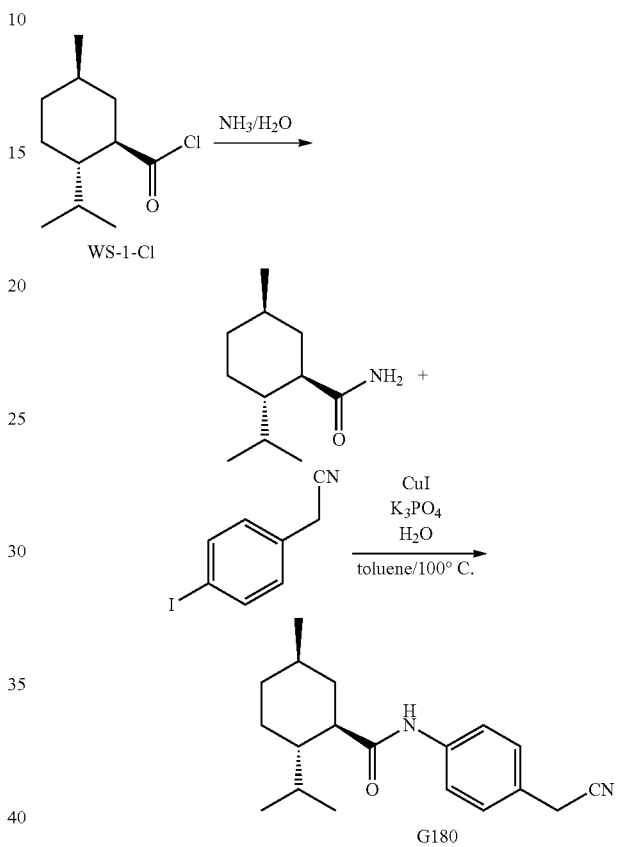

In this reaction pathway, a menthane acid chloride (designated as WS-1-Cl) is reacted with $NH_3/H_2O$ to prepare the menthane carboxamide, which is then reacted with cyanomethylphenyl iodide to produce the desired G-180 product. The coupling reaction has been found to work best in the presence of potassium phosphate. The addition of water to the reaction medium produces consistent results. The reaction is stereospecific, maintaining the (1R,2S,5R)-configuration of the above starting menthanecarboxamide.

Rather than starting from a menthane acid chloride as shown above, a preferred means of obtaining the primary menthane carboxamide material is via hydrolysis of the corresponding nitrile as illustrated below. The menthane nitrile can be obtained from the related alcohol, for example, menthol. It has been found that the reaction of menthane tosylate with sodium cyanide produces a nitrile having opposite stereochemistry at the 1-position from the starting alcohol to produce the menthane tosylate. For example, starting from l-menthol (having 1R,2S,5R configuration) the (1S,2S,5R)-menthane nitrile is produced, i.e., differing in stereochemistry at the C-1 position [*Tetrahedron: Asymmetry* (1996), 7(7), 1967072]. This stereochemistry is maintained through the hydrolysis of the (1S,2S,5R)-menthane nitrile to produce the menthane carboxamide and through the subsequent coupling reaction of the menthane carboxamide with the aryl iodide to produce the final product. The present pathway can thus be used to prepare various isomers including the example below designated herein as a neoisomer, which was prepared starting from l-menthol, a readily available and relatively inexpensive raw material. The neoisomer, i.e., N-[4-(cyanomethyl)phenyl]-(1S,2S,5R)-2-isopropyl-5-methylcyclohexanecarboxamide, unexpectedly is found to have excellent cooling properties.

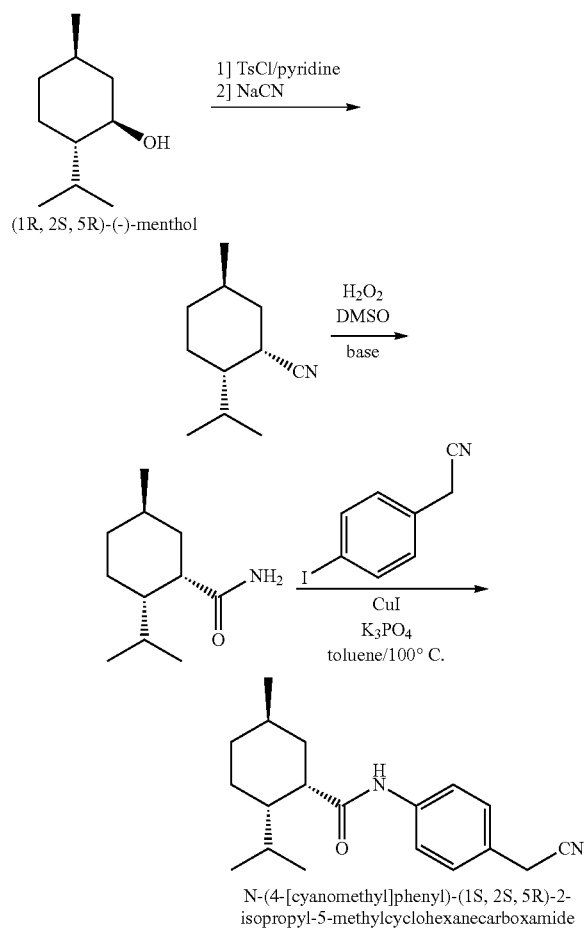

The aryl iodide used in the above examples may be prepared using the following synthetic routes as described in WO 2004/013094 and in *Journal of Medicinal Chemistry* (2005), 48(5), 1336-1343.

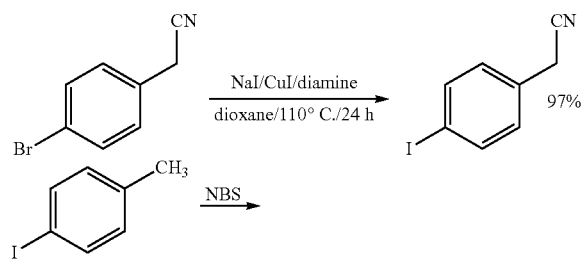

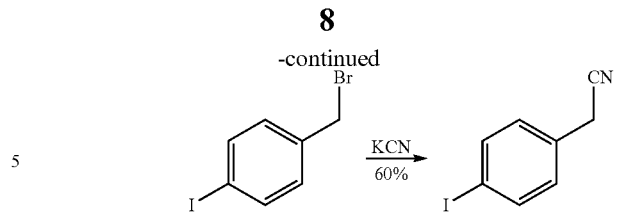

The present chemistry may also be modified to prepare other N-substituted menthanecarboxamide derivatives, including non-aromatic and aliphatic derivatives. For example, the derivative WS-3 (N-ethyl-p-menthan-3-carboxamide) could be prepared by reacting the menthane carboxamide with ethyl iodide in the presence of potassium tert-butoxide as base in diethyl ether containing dicyclohexyl-18-crown-6.

A key advantage of the present reaction scheme is its stereospecificity which enables the preparation of specific isomers or mixtures of isomers. For example, the G-180 and neoisomer materials may be separately prepared and the two isomers combined at a ratio ranging from 1:99 to 99:1. Alternatively, the preparation of any desired mixture of isomers may be conducted by starting with an appropriate proportion of the different starting material isomers. In particular, mixing the two isomers is advantageous in modulating the negative sensory effects from using G-180 alone. In sensory evaluations, panelists have described the sensory effect of G-180 as including a "burning" sensation especially when used at fairly high levels. Mixing the isomers results in an improved overall sensation.

The discovery of the neoisomers of N-aryl substituted menthane carboxamides such as the neo-G-180 neoisomer and its unexpected coolant properties and advantages led to the development of additional synthesis schemes for preparation of neoisomers of other N-substituted menthane carboxamide compounds of the general formula

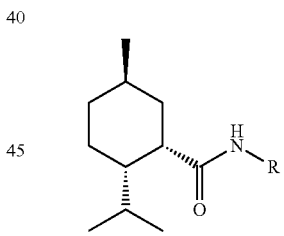

wherein R is selected from linear or branched C1-C8 alkyl, substituted C1-C8 alkyl, substituted or unsubstituted aryl or heteroaryl. The substituents on the alkyl chain, aryl ring or heteroaryl ring include the same substituents on the phenyl ring derivatives described above, i.e., halogen, OH, hydroxy-C1-C4-alkyl, alkoxy, amino, aminoalkyl, $NO_2$, CN, cyano-C1-C4-alkyl, acetyl, $SO_2NH_2$, CHO, $CO_2H$ and C1-C4 alkyl carboxylate.

The (1S,2S,5R)-menthane nitrile (neo-menthyl cyanide) used to obtain the primary menthane carboxamide for the scheme described above, can also be converted to neo-WS-1 via an alternative hydrolysis using e.g., hydrobromic acid. The neo-WS-1 can be used as a precursor to the neoisomer analogs of other known coolants. For example, preparation of neo-menthane carboxamides such as neo-WS-3 and neo-WS-5 and neo-menthane carboxy esters such as neo-WS-4 and neo-WS-30 are shown below.

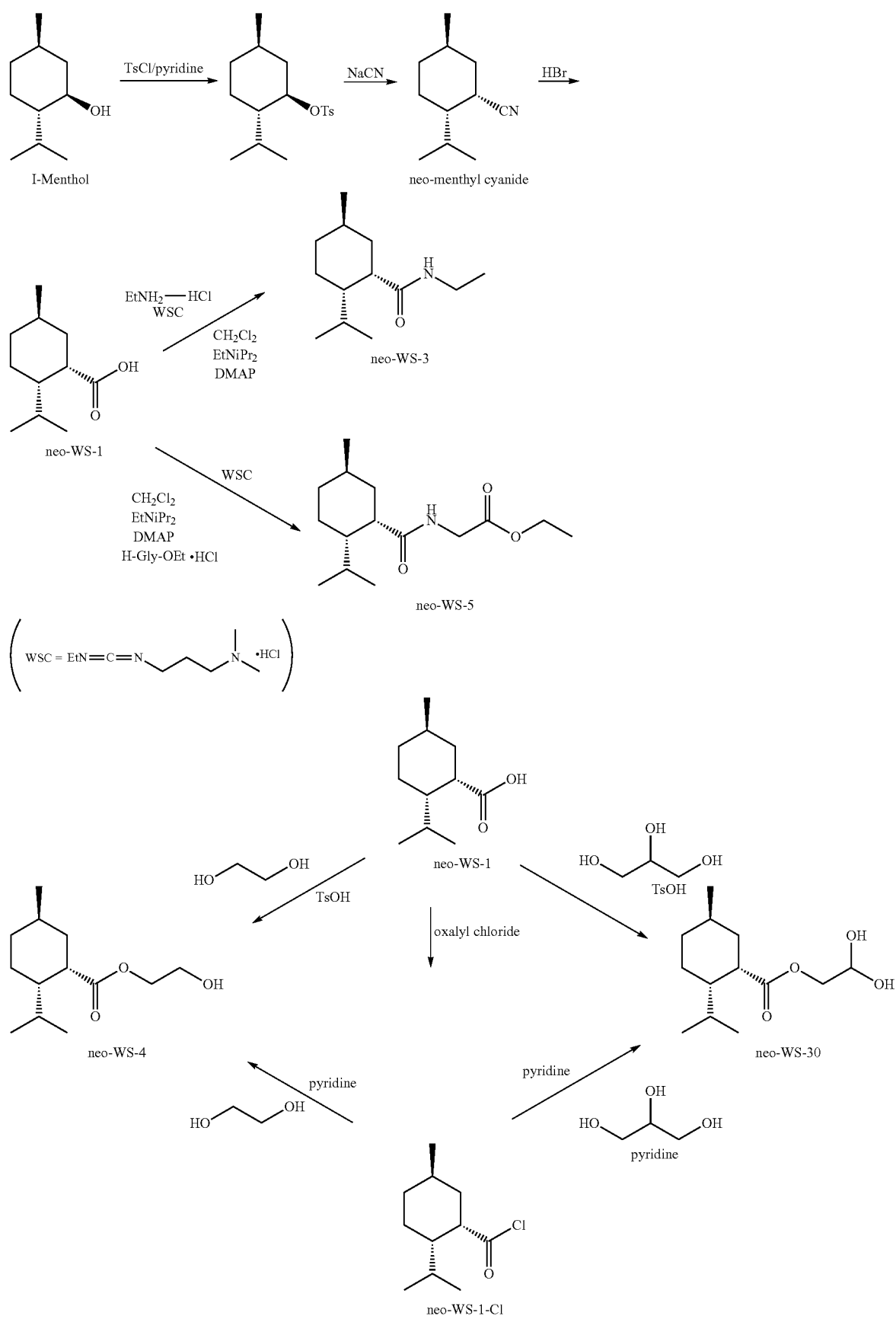

Another set of hydrolysis conditions (e.g., KOH in tert-butanol) can be used to convert the (1S,2S,5R)-menthane nitrile (neo-menthyl cyanide) to WS-1 with (1R,2S,5R) absolute stereochemistry. In this case the nitrile functionality is both hydrolyzed and the C-1 stereocenter is isomerized. This provides an alternate means of producing WS-1, a useful intermediate for the production of many coolants. For example, WS-1 can be converted to known coolants, such as WS-3 and WS-5. This can be done by directly using WS-1 or via the acid chloride (WS-1-Cl) or other activated derivatives as shown below. The corresponding amide can be produced and used as described above as a precursor to N-substituted menthanecarboxamide derivatives.

Further, l-menthol (having the 1R,2S,5R configuration) can be used as a precursor to neo-menthol (having the 1S,2S,5R configuration). The neo-menthol can then be converted to a number of other neo-menthyl analogs including such as esters and ethers that can serve as coolants as shown in the following examples. Neo-menthol can be reacted with a derivatizing agent such as a carboxylic acid, carboxylic acid anhydride, dicarboxylic acid anhydride or carboxylic acid chloride to obtain neo-menthyl esters.

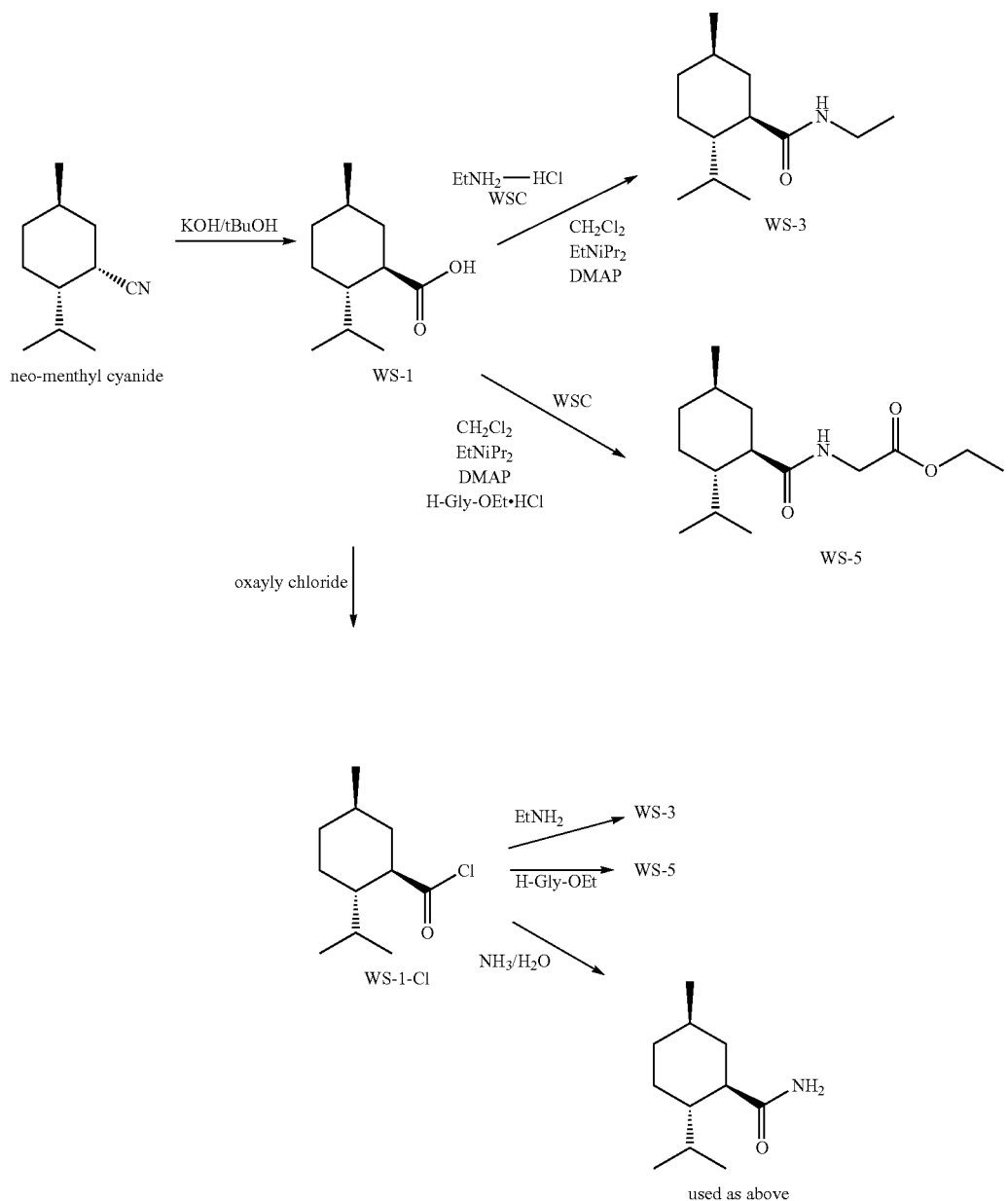

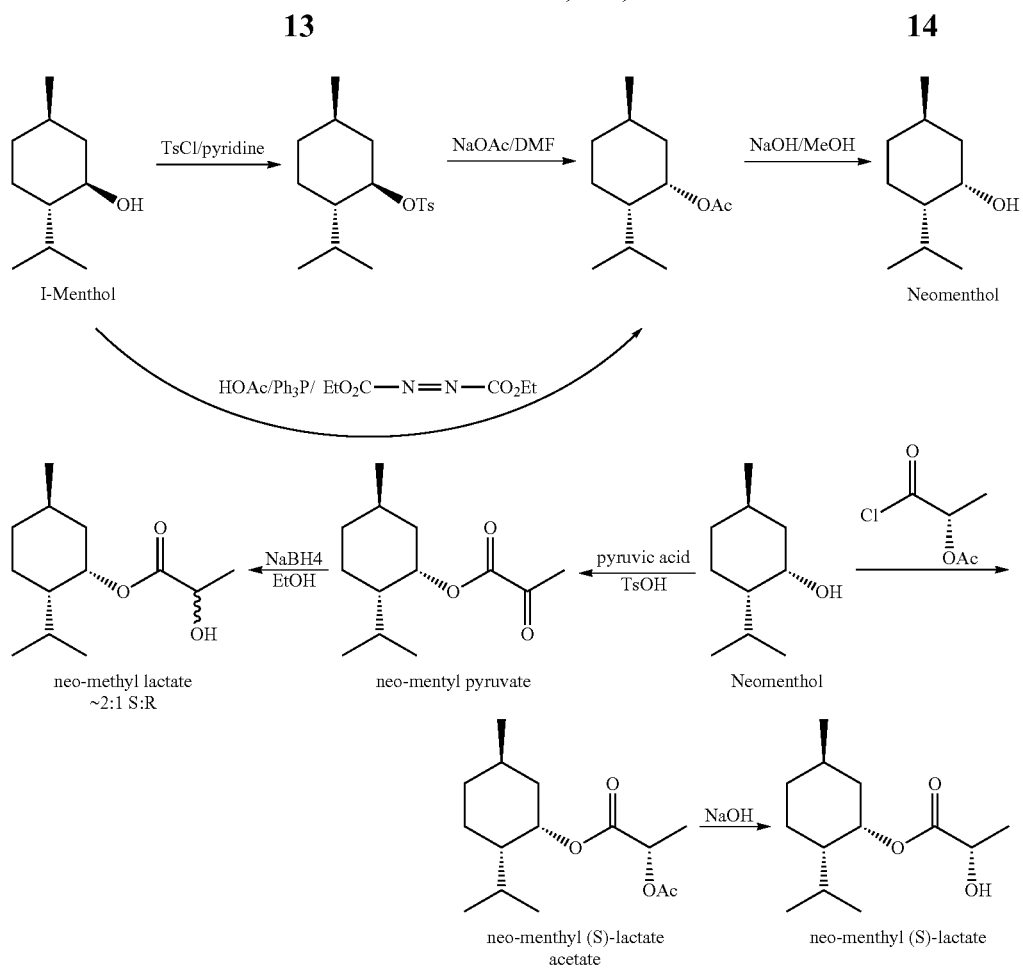

In another example, neo-monomenthyl succinate is prepared using succinic anhydride to avoid making the diester with succinic acid.

188 all assigned to Takasago. For example, the following scheme is used to prepare neo-TK-10.

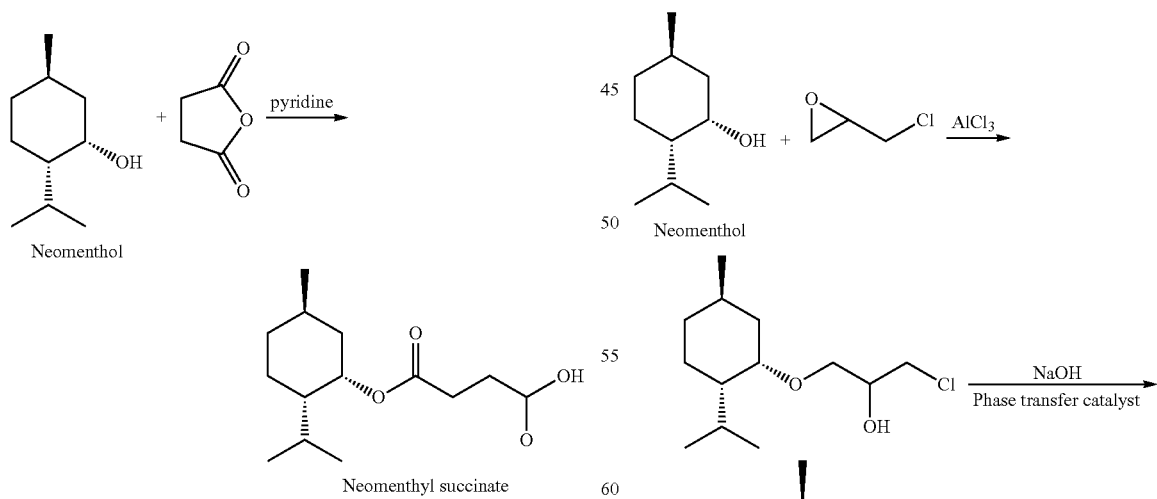

One example of a neo-menthyl ether derivative that can be prepared from neo-menthol is 3-(neo-menthoxy)-1,2-propanediol (neo-TK-10) using schemes similar to those reported for preparation of the l-version of the TK-10 coolant in U.S. Pat. Nos. 4,459,425; 5,608,119; 6,407,293 and 6,515,

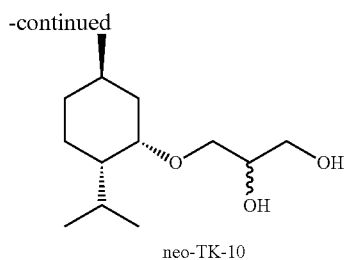

neo-TK-10

The following chemical abbreviations are used in the above preparation schemes:

| | |
|---|---|
| DMF = Dimethyl formamide | DMAP = N,N-Dimethylaminopyridine |
| DMSO = Dimethyl sulfoxide | HOAc = Acetic acid |
| NaOAc = Sodium acetate | NBS = N-Bromosuccinimde |
| TsCl = Tosyl chloride | TsOH = p-Toluenesulfonic acid |

The coolant properties of the materials prepared according to the present methods are evaluated using sensory studies. For example, the menthane carboxamides G-180 and neo-G180 materials were found to provide a cooling sensation similar to that produced by menthol, but longer lasting at significantly lower concentrations. Menthol generally provides an initial high cooling impact, but its effect is somewhat transient in that the cooling sensation drops sharply within a few minutes after use. By contrast, both the G-180 and neoisomer materials provided a sensation that lasted longer than about 15 minutes. The cooling potency of the neoisomer is particularly unexpected, since stereochemistry is a major factor influencing coolant activity and potency for menthol and menthol derivatives as reported in previous studies. [See for example, R. Emberger and R. Hopp (1987), *Specialty Chemicals*, 7(3), 193-201; R. Eccles (1990), *Chemical Senses*, 2, 275-291; S. Rovner (2007), *Chemical & Engineering News*, 85(39), 95-98]. According to the C&EN report, the Givaudan scientists found that the cooling activity of isomers in which the configuration did not match those of l-menthol, specifically at the C-1 position were considerably less potent and in some cases had no activity at all. The effect on activity of these isomers is far more significant than is observed with menthol.

As demonstrated in sensory studies, the neoisomer provided unexpected cooling potency and long lasting sensation. Importantly the sensation provided by the neoisomer had significantly less of the "burning" sensation that has been attributed to the G-180 coolant.

Sensory evaluation studies of coolant activity may be conducted using a methodology patterned after the techniques described in M. C. Meilgaard, et al., *Sensory Evaluation Techniques*, 4$^{th}$ Ed. (2007). A panel of trained sensory experts evaluates cooling sensation experienced after using a product with coolant, for example by brushing with a dentifrice or rinsing with an aqueous rinse. In one protocol, panelists brush teeth with 1.5 grams of a test dentifrice (containing coolant) or control (no coolant) and then expectorate. After brush expectoration, panelists evaluate cooling intensity, assigning a number between 0 (no cooling) to 60 (intense cooling). In a rinse protocol, panelists rinse mouth with 15 ml. of an aqueous rinse and expectorate. After rinse expectoration, panelists evaluate cooling intensity according to the same 0 to 60 scale. Evaluations are conducted various time points, for example, at 5, 15, 30, 45, 60 minute, etc. At each evaluation, panelists are instructed to breathe in through pursed lips and evaluate overall cooling sensation. In this test, a numerical score of 7.5 indicates meaningful or definite cooling.

In one embodiment of the present invention, a neoisomer coolant alone or mixed with the corresponding l-isomer and optionally additional coolants, is incorporated in oral care compositions, typically as part of the flavor system. For example a mixture of G-180 and neo-G-180 are included in a flavor system. The flavor system and other components or ingredients of oral care compositions are described in the following paragraphs along with non-limiting examples. These ingredients include active agents and other orally acceptable carrier materials which are suitable for topical oral administration. By "compatible" is meant that the components of the composition are capable of being commingled without interaction in a manner which would substantially reduce composition stability and/or efficacy. Suitable active agents, carrier or excipient materials are well known in the art. Their selection will depend on desired activity, product form and secondary considerations like taste, cost, and shelf stability, etc.

Suitable carrier materials or components of toothpaste, tooth gel or the like include abrasive materials, sudsing agents, binders, humectants, flavoring and sweetening agents, etc. as disclosed in e.g., U.S. Pat. No. 3,988,433, to Benedict. Carrier materials for biphasic dentifrice formulations are disclosed in U.S. Pat. Nos. 5,213,790; 5,145,666 and 5,281,410 all to Lukacovic et al. and in U.S. Pat. Nos. 4,849,213 and 4,528,180 to Schaeffer. Mouthwash, rinse or mouth spray carrier materials typically include water, flavoring and sweetening agents, etc., as disclosed in, e.g., U.S. Pat. No. 3,988,433 to Benedict. Lozenge carrier materials typically include a candy base; chewing gum carrier materials include a gum base, flavoring and sweetening agents, as in, e.g., U.S. Pat. No. 4,083,955, to Grabenstetter et al. Sachet carrier materials typically include a sachet bag, flavoring and sweetening agents. For subgingival gels used for delivery of actives into the periodontal pockets or around the periodontal pockets, a "subgingival gel carrier" is chosen as disclosed in, e.g. U.S. Pat. Nos. 5,198,220 and 5,242,910 both to Damani.

In one embodiment, the compositions of the subject invention are in the form of dentifrices, such as toothpastes, tooth gels and tooth powders. Components of such toothpaste and tooth gels generally include one or more of a dental abrasive (from about 6% to about 50%), a surfactant (from about 0.5% to about 10%), a thickening agent (from about 0.1% to about 5%), a humectant (from about 10% to about 55%), a flavoring agent (from about 0.04% to about 2%), a sweetening agent (from about 0.1% to about 3%), a coloring agent (from about 0.01% to about 0.5%) and water (from about 2% to about 45%). Such toothpaste or tooth gel may also include one or more of an anticaries agent (from about 0.05% to about 0.3% as fluoride ion) and an anticalculus agent (from about 0.1% to about 13%). Tooth powders, of course, contain substantially all non-liquid components.

Other embodiments of the subject invention are liquid products, including mouthwashes or rinses, mouth sprays, dental solutions and irrigation fluids. Components of such mouthwashes and mouth sprays typically include one or more of water (from about 45% to about 95%), ethanol (from about 0% to about 25%), a humectant (from about 0% to about 50%), a surfactant (from about 0.01% to about 7%), a flavoring agent (from about 0.04% to about 2%), a sweetening agent (from about 0.1% to about 3%), and a coloring agent (from about 0.001% to about 0.5%). Such mouthwashes and mouth sprays may also include one or more of an anticaries agent (from about 0.05% to about 0.3% as fluoride ion) and an anticalculus agent (from about 0.1% to about 3%). Components of dental solutions generally include one or more of water (from about 90% to about 99%), preservative (from about 0.01% to about 0.5%), thickening agent (from 0% to about 5%), flavoring agent (from about 0.04% to about 2%), sweetening agent (from about 0.1% to about 3%), and surfactant (from 0% to about 5%).

The compositions of the present invention may also be in the form of non-abrasive gels and subgingival gels, which may be aqueous or non-aqueous. In still another aspect, the invention provides a dental implement impregnated with the present composition. The dental implement comprises an implement for contact with teeth and other tissues in the oral cavity, said implement being impregnated with the present composition. The dental implement can be impregnated fibers including dental floss or tape, chips, strips, films and polymer fibers.

Flavor System

The neoisomer menthane coolants and optionally other coolants including menthol and synthetic coolants described above such as G-180, would typically be part of a flavor system, preferably one that effectively masks any unpleasant taste and sensations due to certain components of the composition such as antimicrobial actives or peroxide. Pleasant tasting compositions improve user compliance to prescribed or recommended use of oral care products. The present flavor system may also comprise traditional flavor components, in particular those that have been found to be relatively stable in the presence of usual oral care product carrier materials or excipients. The combination of the selected flavoring components with the coolant(s) provides a high-impact refreshing sensation with a well-rounded flavor profile.

The oral care composition will comprise from about 0.001% to 1.5% by weight of the synthetic menthane coolant(s). Mixtures of the neoisomer and l-isomer of the menthane coolant, for example neo-G-180 and G-180, will range from about 1:99 to about 99:1. If present, typically the level of menthol in the final composition ranges from about 0.010% to about 1.0%.

In addition to the coolant(s) above, the flavor system may comprise additional flavor ingredients including but not limited to peppermint oil, corn mint oil, spearmint oil, oil of wintergreen, clove bud oil, cassia, sage, parsley oil, marjoram, lemon, lime, orange, cis-jasmone, 2,5-dimethyl-4-hydroxy-3 (2H)-furanone, 5-ethyl-3-hydroxy-4-methyl-2(5H)-furanone, vanillin, ethyl vanillin, anisaldehyde, 3,4-methylenedioxybenzaldehyde, 3,4-dimethoxybenzaldehyde, 4-hydroxybenzaldehyde, 2-methoxybenzaldehyde, benzaldehyde; cinnamaldehyde, hexyl cinnamaldehyde, alpha-methyl cinnamaldehyde, ortho-methoxy cinnamaldehyde, alpha-amyl cinnamaldehydepropenyl guaethol, heliotropine, 4-cis-heptenal, diacetyl, methyl-ρ-tert-butyl phenyl acetate, menthol, methyl salicylate, ethyl salicylate, 1-menthyl acetate, oxanone, alpha-irisone, methyl cinnamate, ethyl cinnamate, butyl cinnamate, ethyl butyrate, ethyl acetate, methyl anthranilate, iso-amyl acetate, iso-amyl butyrate, allyl caproate, eugenol, eucalyptol, thymol, cinnamic alcohol, octanol, octanal, decanol, decanal, phenylethyl alcohol, benzyl alcohol, alpha-terpineol, linalool, limonene, citral, maltol, ethyl maltol, anethole, dihydroanethole, carvone, menthone, β-damascenone, ionone, gamma decalactone, gamma nonalactone, gamma undecalactone and mixtures thereof. Generally suitable flavoring ingredients are those containing structural features and functional groups that are less prone to redox reactions. These include derivatives of flavor chemicals that are saturated or contain stable aromatic rings or ester groups. Also suitable are flavor chemicals that may undergo some oxidation or degradation without resulting in a significant change in the flavor character or profile. The flavor ingredients may be supplied in the composition as single or purified chemicals or by addition of natural oils or extracts that have preferably undergone a refining treatment to remove components that are relatively unstable and may degrade and alter the desired flavor profile, resulting in a less acceptable product from an organoleptic standpoint. Flavoring agents are generally used in the compositions at levels of from about 0.001% to about 5%, by weight of the composition.

The flavor system will typically include a sweetening agent. Suitable sweeteners include those well known in the art, including both natural and artificial sweeteners. Some suitable water-soluble sweeteners include monosaccharides, disaccharides and polysaccharides such as xylose, ribose, glucose (dextrose), mannose, galactose, fructose (levulose), sucrose (sugar), maltose, invert sugar (a mixture of fructose and glucose derived from sucrose), partially hydrolyzed starch, corn syrup solids, dihydrochalcones, monellin, steviosides, and glycyrrhizin. Suitable water-soluble artificial sweeteners include soluble saccharin salts, i.e., sodium or calcium saccharin salts, cyclamate salts, the sodium, ammonium or calcium salt of 3,4-dihydro-6-methyl-1,2,3-oxathiazine-4-one-2,2-dioxide, the potassium salt of 3,4-dihydro-6-methyl-1,2,3-oxathiazine-4-one-2,2-dioxide (acesulfame-K), the free acid form of saccharin, and the like. Other suitable sweeteners include dipeptide based sweeteners, such as L-aspartic acid derived sweeteners, such as L-aspartyl-L-phenylalanine methyl ester (aspartame) and materials described in U.S. Pat. No. 3,492,131, L-alpha-aspartyl-N-(2,2,4,4-tetramethyl-3-thietanyl)-D-alaninamide hydrate, methyl esters of L-aspartyl-L-phenylglycerin and L-aspartyl-L-2,5,dihydrophenyl-glycine, L-aspartyl-2,5-dihydro-L-phenylalanine, L-aspartyl-L-(1-cyclohexylen)-alanine, and the like. Water-soluble sweeteners derived from naturally occurring water-soluble sweeteners, such as a chlorinated derivative of ordinary sugar (sucrose), known, for example, under the product description of sucralose as well as protein based sweeteners such as thaumatoccous danielli (Thaumatin I and II) can be used. A composition preferably contains from about 0.1% to about 10% of sweetener, preferably from about 0.1% to about 1%, by weight of the composition.

In addition the flavor system may include salivating agents, warming agents, and numbing agents. These agents are present in the compositions at a level of from about 0.001% to about 10%, preferably from about 0.1% to about 1%, by weight of the composition. Suitable salivating agents include Jambu® manufactured by Takasago. Suitable numbing agents include benzocaine, lidocaine, clove bud oil, and ethanol. Examples of warming agents include ethanol, capsicum and nicotinate esters, such as benzyl nicotinate. Use of agents with warming effects may of course alter the cooling effect of coolants and will need to be considered, particularly in optimizing the level of coolants.

Calcium Ion Source

The present compositions may also include a calcium ion source. As described in commonly assigned U.S. Application No. 61/003,863 calcium ions provide enhanced activity of coolants in terms of onset, intensity or impact and duration. It has also been found that the potentiating effect of calcium ions on coolants, particularly the synthetic menthane carboxamide derivatives is further enhanced in the presence of menthol. The source of calcium ions may be any physiologically acceptable calcium compound including inorganic or organic salts such as halides (chloride, bromide, iodide, fluoride), nitrate, nitrite, phosphate, pyrophosphate, polyphosphate, sulfate, carbonate, hypochlorite, formate, acetate, citrate, lactate, maleate, gluconate, tartrate, glycerophosphate, butyrate, isobutyrate, oxalate, peptide, phosphopeptide or from oxides or hydroxides. The calcium ion source may be water soluble, sparingly-soluble or insoluble and can provide a minimum level of at least about 50 ppm calcium ions for potentiating activity. The level of the calcium ion source is of course also dependent on secondary considerations such as aesthetics and stability of the compositions. Some calcium compounds may alter the overall taste of the composition, for example being described as "chalky" and would thus not be desirable at levels that produce such effects.

Fluoride Source

It is common to have a fluoride compound present in dentifrices and other oral compositions in an amount sufficient to give a fluoride ion concentration in the composition of from about 0.0025% to about 5.0% by weight, preferably from about 0.005% to about 2.0% by weight to provide anticaries effectiveness. As discussed above, prevention of caries is essential for overall tooth health and integrity. A wide variety of fluoride ion-yielding materials can be employed as sources of soluble fluoride in the present compositions. Examples of suitable fluoride ion-yielding materials are found in U.S. Pat. No. 3,535,421 to Briner et al. and U.S. Pat. No. 3,678,154 to Widder et al. Representative fluoride ion sources include: stannous fluoride, sodium fluoride, potassium fluoride, amine fluoride, sodium monofluorophosphate, indium fluoride and many others.

Antimicrobial Agent

The present compositions may include an antimicrobial agent, such as a quaternary ammonium antimicrobial agent to provide bactericidal efficacy, i.e., effectiveness in killing, and/or altering metabolism, and/or suppressing the growth of, microorganisms which cause topically-treatable infections and diseases of the oral cavity, such as plaque, caries, gingivitis, and periodontal disease. The antimicrobial quaternary ammonium compounds useful in the compositions of the present invention include those in which one or two of the substitutes on the quaternary nitrogen has a carbon chain length (typically alkyl group) from about 8 to about 20, typically from about 10 to about 18 carbon atoms while the remaining substitutes (typically alkyl or benzyl group) have a lower number of carbon atoms, such as from about 1 to about 7 carbon atoms, typically methyl or ethyl groups. Dodecyl trimethyl ammonium bromide, tetradecylpyridinium chloride, domiphen bromide, N-tetradecyl-4-ethyl pyridinium chloride, dodecyl dimethyl (2-phenoxyethyl) ammonium bromide, benzyl dimethoylstearyl ammonium chloride, cetylpyridinium chloride, quaternized 5-amino-1,3-bis(2-ethyl-hexyl)-5-methyl hexahydropyrimidine, benzalkonium chloride, benzethonium chloride and methyl benzethonium chloride are exemplary of typical quaternary ammonium antibacterial agents. Other compounds are bis[4-(R-amino)-1-pyridinium] alkanes as disclosed in U.S. Pat. No. 4,206,215, Jun. 3, 1980 to Bailey. The pyridinium compounds are the preferred quaternary ammonium compounds, particularly preferred being cetylpyridinium, or tetradecylpyridinium halide salts (i.e., chloride, bromide, fluoride and iodide). Most preferred is cetylpyridinium chloride. The quaternary ammonium antimicrobial agents are included in the present invention at levels of at least about 0.035%, preferably from about 0.045% to about 1.0%, more preferably from about 0.05% to about 0.10% by weight of the composition.

The present compositions may comprise a metal ion source that provides stannous ions, zinc ions, copper ions, or mixtures thereof as antimicrobial agent. The metal ion source can be a soluble or a sparingly soluble compound of stannous, zinc, or copper with inorganic or organic counter ions. Examples include the fluoride, chloride, chlorofluoride, acetate, hexafluorozirconate, sulfate, tartrate, gluconate, citrate, malate, glycinate, pyrophosphate, metaphosphate, oxalate, phosphate, carbonate salts and oxides of stannous, zinc, and copper.

Stannous, zinc and copper ions have been found to help in the reduction of gingivitis, plaque, sensitivity, and improved breath benefits. An effective amount is defined as from at least about 50 ppm to about 20,000 ppm metal ion of the total composition, preferably from about 500 ppm to about 15,000 ppm. More preferably, metal ions are present in an amount from about 3,000 ppm to about 13,000 ppm and even more preferably from about 5,000 ppm to about 10,000 ppm. This is the total amount of metal ions (stannous, zinc, copper and mixtures thereof) for delivery to the tooth surface.

Dentifrices containing stannous salts, particularly stannous fluoride and stannous chloride, are described in U.S. Pat. No. 5,004,597 to Majeti et al. Other descriptions of stannous salts are found in U.S. Pat. No. 5,578,293 issued to Prencipe et al. and in U.S. Pat. No. 5,281,410 issued to Lukacovic et al. Other ingredients needed to stabilize the stannous may be included, such as the ingredients described in Majeti et al. and Prencipe et al.

The preferred stannous salts are stannous fluoride and stannous chloride dihydrate. Other suitable stannous salts include stannous acetate, stannous tartrate and sodium stannous citrate. Examples of suitable zinc ion sources are zinc oxide, zinc sulfate, zinc chloride, zinc citrate, zinc lactate, zinc gluconate, zinc malate, zinc tartrate, zinc carbonate, zinc phosphate, and other salts listed in U.S. Pat. No. 4,022,880. Zinc citrate and zinc lactate are particularly preferred. Examples of suitable copper ion sources are listed in U.S. Pat. No. 5,534,243. The combined metal ion source(s) will be present in an amount of from about 0.05% to about 11%, by weight of the final composition. Preferably, the metal ion sources are present in an amount of from about 0.5 to about 7%, more preferably from about 1% to about 5%. Preferably, the stannous salts may be present in an amount of from about 0.1 to about 7%, more preferably from about 1% to about 5%, and most preferably from about 1.5% to about 3% by weight of the total composition. The amount of zinc or copper salts used in the present invention ranges from about 0.01 to about 5%, preferably from about 0.05 to about 4%, more preferably from about 0.1 to about 3.0%.

The present invention may also include other antimicrobial agents including non-cationic antimicrobial agents such as halogenated diphenyl ethers, phenolic compounds including phenol and its homologs, mono and poly-alkyl and aromatic halophenols, resorcinol and its derivatives, xylitol, bisphenolic compounds and halogenated salicylanilides, benzoic esters, and halogenated carbanilides. Also useful antimicrobials are enzymes, including endoglycosidase, papain, dextranase, mutanase, and mixtures thereof. Such agents are disclosed in U.S. Pat. No. 2,946,725, Jul. 26, 1960, to Norris et al. and in U.S. Pat. No. 4,051,234 to Gieske et al. Examples of other antimicrobial agents include chlorhexidine, triclosan, triclosan monophosphate, and flavor oils such as thymol. Triclosan and other agents of this type are disclosed in Parran, Jr. et al., U.S. Pat. No. 5,015,466, and U.S. Pat. No. 4,894,220 to Nabi et al. These agents may be present at levels of from about 0.01% to about 1.5%, by weight of the dentifrice composition.

Anticalculus Agent

The present compositions may optionally include an anticalculus agent, such as a pyrophosphate salt as a source of pyrophosphate ion. The pyrophosphate salts useful in the present compositions include the mono-, di- and tetraalkali metal pyrophosphate salts and mixtures thereof. Disodium dihydrogen pyrophosphate ($Na_2H_2P_2O_7$), sodium acid pyrophosphate, tetrasodium pyrophosphate ($Na_4P_2O_7$), and tetrapotassium pyrophosphate ($K_4P_2O_7$) in their unhydrated as well as hydrated forms are the preferred species. In compositions of the present invention, the pyrophosphate salt may be present in one of three ways: predominately dissolved, predominately undissolved, or a mixture of dissolved and undissolved pyrophosphate.

Compositions comprising predominately dissolved pyrophosphate refer to compositions where at least one pyrophosphate ion source is in an amount sufficient to provide at least about 0.025% free pyrophosphate ions. The amount of free pyrophosphate ions may be from about 1% to about 15%, from about 1.5% to about 10% in one embodiment, and from about 2% to about 6% in another embodiment. Free pyrophosphate ions may be present in a variety of protonated states depending on the pH of the composition.

Compositions comprising predominately undissolved pyrophosphate refer to compositions containing no more than about 20% of the total pyrophosphate salt dissolved in the composition, preferably less than about 10% of the total pyrophosphate dissolved in the composition. Tetrasodium pyrophosphate salt is a preferred pyrophosphate salt in these compositions. Tetrasodium pyrophosphate may be the anhydrous salt form or the decahydrate form, or any other species stable in solid form in the dentifrice compositions. The salt is in its solid particle form, which may be its crystalline and/or amorphous state, with the particle size of the salt preferably being small enough to be aesthetically acceptable and readily soluble during use. The amount of pyrophosphate salt useful in making these compositions is any tartar control effective amount, generally from about 1.5% to about 15%, preferably from about 2% to about 10%, and most preferably from about 3% to about 8%, by weight of the dentifrice composition.

Compositions may also comprise a mixture of dissolved and undissolved pyrophosphate salts. Any of the above mentioned pyrophosphate salts may be used.

The pyrophosphate salts are described in more detail in *Kirk-Othmer Encyclopedia of Chemical Technology*, Third Edition, Volume 17, Wiley-Interscience Publishers (1982).

Optional agents to be used in place of or in combination with the pyrophosphate salt include such known materials as longer chain (3 or more) polyphosphates including tripolyphosphate, tetrapolyphosphate and hexametaphosphate; synthetic anionic polymers, including polyacrylates and copolymers of maleic anhydride or acid and methyl vinyl ether (e.g., Gantrez), as described, for example, in U.S. Pat. No. 4,627,977, to Gaffar et al. as well as, e.g., polyamino propane sulfonic acid (AMPS), diphosphonates (e.g., EHDP; AHP), polypeptides (such as polyaspartic and polyglutamic acids), and mixtures thereof.

Other Active Agents

Still another active agent that may be included in the present compositions is a tooth bleaching active selected from the group consisting of peroxides, perborates, percarbonates, peroxyacids, persulfates, and combinations thereof. Suitable peroxide compounds include hydrogen peroxide, urea peroxide, calcium peroxide, sodium peroxide, zinc peroxide and mixtures thereof. A preferred percarbonate is sodium percarbonate. Preferred persulfates are oxones.

Preferred peroxide sources for use in dentifrice formulations are calcium peroxide and urea peroxide. Hydrogen peroxide and urea peroxide are preferred for use in mouthrinse formulations. The following amounts represent the amount of peroxide raw material, although the peroxide source may contain ingredients other than the peroxide raw material. The present composition may contain from about 0.01% to about 30%, preferably from about 0.1% to about 10%, and more preferably from about 0.5% to about 5% of a peroxide source, by weight of the composition.

In addition to whitening, the peroxide also provides other benefits to the oral cavity. It has long been recognized that hydrogen peroxide and other peroxygen-compounds are effective in curative and/or prophylactic treatments with respect to caries, dental plaque, gingivitis, periodontitis, mouth odor, recurrent aphthous ulcers, denture irritations, orthodontic appliance lesions, postextraction and postperiodontal surgery, traumatic oral lesions and mucosal infections, herpetic stomatitis and the like. Peroxide-containing agents in the oral cavity exert a chemomechanical action generating thousands of tiny oxygen bubbles produced by interaction with tissue and salivary enzymes. The swishing action of a mouthrinse enhances this inherent chemomechanical action. Such action has been recommended for delivery of other agents into infected gingival crevices. Peroxide mouthrinses thus prevent colonization and multiplication of anaerobic bacteria known to be associated with periodontal disease.

Another optional active agent that may be added to the present compositions is a dentinal desensitizing agent to control hypersensitivity, such as salts of potassium, calcium, strontium and tin including nitrate, chloride, fluoride, phosphates, pyrophosphate, polyphosphate, citrate, oxalate and sulfate.

Tooth Substantive Agent

The present invention may include a tooth substantive agent such as polymeric surface active agents (PMSA's), which are polyelectrolytes, more specifically anionic polymers. The PMSA's contain anionic groups, e.g., phosphate, phosphonate, carboxy, or mixtures thereof, and thus, have the capability to interact with cationic or positively charged entities. The "mineral" descriptor is intended to convey that the surface activity or substantivity of the polymer is toward mineral surfaces such as calcium phosphate minerals in teeth.

Tooth substantive agents provide many benefits including providing protection and resistance of teeth against erosion and wear derived from binding of calcium minerals in teeth (hydroxyapatite) and/or deposition on the tooth surface of a protective surface coating. Dental erosion is a permanent loss of tooth substance from the surface due to the action of chemicals, such as harsh abrasives and acids. The protective surface coating provides control of tooth surface characteristics including modification of surface hydrophilic and hydrophobic properties and resistance to acid attack. The tooth substantive agents may also provide desired surface conditioning effects including: 1) effective desorption of portions of undesirable adsorbed pellicle proteins, in particular those associated with tooth stain binding, calculus development and attraction of undesirable microbial species and 2) maintaining surface conditioning effects and control of pellicle film for extended periods following product use, including post brushing and throughout more extended periods. The effect of modifying the surface hydrophilic and hydrophobic properties can be measured in terms of changes in water contact angles, a relative decrease indicating a more hydrophilic surface and a relative increase indicating a more hydrophobic surface. Many of the tooth substantive agents also provide tartar control or antistain/whitening or surface conditioning activities, hence providing multiple clinical actions in improving overall health and structure of teeth as well as appearance and tactile impression of teeth. It is believed the tooth substantive agents provide a stain prevention benefit because of their reactivity or substantivity to mineral surfaces, resulting in desorption of portions of undesirable adsorbed pellicle proteins, in particular those associated with binding color bodies that stain teeth, calculus development and attraction of undesirable microbial species. The retention of these agents on teeth can also prevent stains from accruing due to disruption of binding sites of color bodies on tooth surfaces.

Suitable examples of PMSA tooth substantive agents are polyelectrolytes such as condensed phosphorylated polymers; polyphosphonates; copolymers of phosphate- or phosphonate-containing monomers or polymers with other monomers such as ethylenically unsaturated monomers and amino acids or with other polymers such as proteins, polypeptides, polysaccharides, poly(acrylate), poly(acrylamide), poly(methacrylate), poly(ethacrylate), poly(hydroxyalkylmethacrylate), poly(vinyl alcohol), poly(maleic anhydride), poly(maleate)poly(amide), poly(ethylene amine), poly(ethylene glycol), poly(propylene glycol), poly(vinyl acetate) and poly(vinyl benzyl chloride); polycarboxylates and carboxy-substituted polymers; and mixtures thereof. Suitable polymeric mineral surface active agents include the carboxy-substituted alcohol polymers described in U.S. Pat. Nos. 5,292,501; 5,213,789, 5,093,170; 5,009,882; and 4,939,284; all to Degenhardt et al. and the diphosphonate-derivatized polymers in U.S. Pat. No. 5,011,913 to Benedict et al; the synthetic anionic polymers including polyacrylates and copolymers of maleic anhydride or acid and methyl vinyl ether (e.g., Gantrez), as described, for example, in U.S. Pat. No. 4,627,977, to Gaffar et al. A preferred polymer is diphosphonate modified polyacrylic acid. Polymers with activity must have sufficient surface binding propensity to desorb pellicle proteins and remain affixed to enamel surfaces. For tooth surfaces, polymers with end or side chain phosphate or phosphonate functions are preferred although other polymers with mineral binding activity may prove effective depending upon adsorption affinity.

Additional examples of suitable phosphonate containing polymeric mineral surface active agents include the geminal diphosphonate polymers disclosed as anticalculus agents in U.S. Pat. No. 4,877,603 to Degenhardt et al; phosphonate group containing copolymers disclosed in U.S. Pat. No. 4,749,758 to Dursch et al. and in GB 1,290,724 (both assigned to Hoechst) suitable for use in detergent and cleaning compositions; and the copolymers and cotelomers disclosed as useful for applications including scale and corrosion inhibition, coatings, cements and ion-exchange resins in U.S. Pat. No. 5,980,776 to Zakikhani et al. and U.S. Pat. No. 6,071,434 to Davis et al. Additional polymers include the water-soluble copolymers of vinylphosphonic acid and acrylic acid and salts thereof disclosed in GB 1,290,724 wherein the copolymers contain from about 10% to about 90% by weight vinylphosphonic acid and from about 90% to about 10% by weight acrylic acid, more particularly wherein the copolymers have a weight ratio of vinylphosphonic acid to acrylic acid of 70% vinylphosphonic acid to 30% acrylic acid; 50% vinylphosphonic acid to 50% acrylic acid; or 30% vinylphosphonic acid to 70% acrylic acid. Other suitable polymers include the water soluble polymers disclosed by Zakikhani and Davis prepared by copolymerizing diphosphonate or polyphosphonate monomers having one or more unsaturated C=C bonds (e.g., vinylidene-1,1-diphosphonic acid and 2-(hydroxyphosphinyl)ethylidene-1,1-diphosphonic acid), with at least one further compound having unsaturated C=C bonds (e.g., acrylate and methacrylate monomers). Suitable polymers include the diphosphonate/acrylate polymers supplied by Rhodia under the designation ITC 1087 (Average MW 3000-60,000) and Polymer 1154 (Average MW 6000-55,000).

A preferred PMSA is a polyphosphate. A polyphosphate is generally understood to consist of two or more phosphate molecules arranged primarily in a linear configuration, although some cyclic derivatives may be present. Although pyrophosphates (n=2) are technically polyphosphates, the polyphosphates desired are those having around three or more phosphate groups so that surface adsorption at effective concentrations produces sufficient non-bound phosphate functions, which enhance the anionic surface charge as well as hydrophilic character of the surfaces. The inorganic polyphosphate salts desired include tripolyphosphate, tetrapolyphosphate and hexametaphosphate, among others. Polyphosphates larger than tetrapolyphosphate usually occur as amorphous glassy materials. Preferred in this invention are the linear polyphosphates having the formula:

$$XO(XPO_3)_nX,$$

wherein X is sodium, potassium or ammonium and n averages from about 3 to about 125. Preferred polyphosphates are those having n averaging from about 6 to about 21, such as those commercially known as Sodaphos (n≈6), Hexaphos (n≈13), and Glass H (n≈21) and manufactured by FMC Corporation and Astaris. These polyphosphates may be used alone or in combination. Polyphosphates are susceptible to hydrolysis in high water formulations at acid pH, particularly below pH 5. Thus it is preferred to use longer-chain polyphosphates, in particular Glass H with an average chain length of about 21. It is believed such longer-chain polyphosphates when undergoing hydrolysis produce shorter-chain polyphosphates which are still effective to deposit onto teeth and provide a stain preventive benefit. In addition to creating the surface modifying effects, the tooth substantive agent may also function to solubilize insoluble salts. For example, Glass H has been found to solubilize insoluble stannous salts. Thus, in compositions containing stannous fluoride for example, Glass H contributes to decreasing the stain promoting effect of stannous.

Other polyphosphorylated compounds may be used in addition to or instead of the polyphosphate, in particular polyphosphorylated inositol compounds such as phytic acid, myo-inositol pentakis(dihydrogen phosphate); myo-inositol tetrakis(dihydrogen phosphate), myo-inositol trikis(dihydrogen phosphate), and an alkali metal, alkaline earth metal or ammonium salt thereof. Preferred herein is phytic acid, also known as myo-inositol 1,2,3,4,5,6-hexakis (dihydrogen phosphate) or inositol hexaphosphoric acid, and its alkali metal, alkaline earth metal or ammonium salts. Herein, the term "phytate" includes phytic acid and its salts as well as the other polyphosphorylated inositol compounds.

Still other surface active organophosphate compounds useful as tooth substantive agents include phosphate mono-, di- or triesters represented by the following general structure:

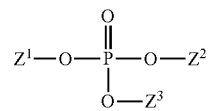

wherein $Z^1$, $Z^2$, or $Z^3$ may be identical or different, at least one being an organic moiety, preferably selected from linear or branched, alkyl or alkenyl group of from 6 to 22 carbon atoms, optionally substituted by one or more phosphate groups; alkoxylated alkyl or alkenyl, (poly)saccharide, polyol or polyether group.

Some preferred agents include alkyl or alkenyl phosphate esters represented by the following structure:

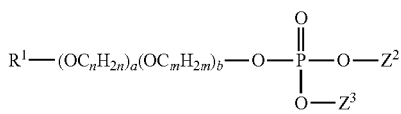

wherein $R^1$ represents a linear or branched, alkyl or alkenyl group of from 6 to 22 carbon atoms, optionally substituted by one or more phosphate groups; n and m, are individually and separately, 2 to 4, and a and b, individually and separately, are 0 to 20; $Z^2$ and $Z^3$ may be identical or different, each represents hydrogen, alkali metal, ammonium, protonated alkyl amine or protonated functional alkyl amine such as an alkanolamine, or a $R^1$—$(OC_nH_{2n})_a(OC_mH_{2m})_b$— group. Examples of suitable agents include alkyl and alkyl(poly)alkoxy phosphates such as lauryl phosphate (tradenames MAP 230K and MAP 230T from Croda); PPG5 ceteareth-10 phosphate (available from Croda under the tradename Crodaphos SG); Laureth-1 phosphate (tradenames MAP L210 from Rhodia, Phosten HLP-1 from Nikkol Chemical or Sunmaep L from Sunjin); Laureth-3 phosphate (tradenames MAP L130 from Rhodia or Foamphos L-3 from Alzo or Emphiphos DF 1326 from Huntsman Chemical); Laureth-9 phosphate (tradename Foamphos L-9 from Alzo); Trilaureth-4 phosphate (tradenames Hostaphat KL 340D from Clariant or TLP-4 from Nikkol Chemical); C12-18 PEG 9 phosphate (tradename Crafol AP261 from Cognis); Sodium dilaureth-10 phosphate (tradename DLP-10 from Nikkol Chemical). Particularly preferred agents are polymeric, for example those containing repeating alkoxy groups as the polymeric portion, in particular 3 or more ethoxy, propoxy isopropoxy or butoxy groups.

Additional suitable polymeric organophosphate agents include dextran phosphate, polyglucoside phosphate, alkyl polyglucoside phosphate, polyglyceryl phosphate, alkyl polyglyceryl phosphate, polyether phosphates and alkoxylated polyol phosphates. Some specific examples are PEG phosphate, PPG phosphate, alkyl PPG phosphate, PEG/PPG phosphate, alkyl PEG/PPG phosphate, PEG/PPG/PEG phosphate, dipropylene glycol phosphate, PEG glyceryl phosphate, PBG (polybutylene glycol) phosphate, PEG cyclodextrin phosphate, PEG sorbitan phosphate, PEG alkyl sorbitan phosphate, and PEG methyl glucoside phosphate.

Suitable non-polymeric phosphates include alkyl mono glyceride phosphate, alkyl sorbitan phosphate, alkyl methyl glucoside phosphate, alkyl sucrose phosphates.

The amount of tooth substantive agent will typically be from about 0.1% to about 35% by weight of the total oral composition. In dentifrice formulations, the amount is preferably from about 2% to about 30%, more preferably from about 5% to about 25%, and most preferably from about 6% to about 20%. In mouthrinse compositions, the amount of tooth substantive agent is preferably from about 0.1% to 5% and more preferably from about 0.5% to about 3%.

Chelating Agents

Another optional agent is a chelating agent, also called sequestrants, such as gluconic acid, tartaric acid, citric acid and pharmaceutically-acceptable salts thereof. Chelating agents are able to complex calcium found in the cell walls of the bacteria. Chelating agents can also disrupt plaque by removing calcium from the calcium bridges which help hold this biomass intact. However, it is not desired to use a chelating agent which has an affinity for calcium that is too high, as this may result in tooth demineralization, which is contrary to the objects and intentions of the present invention. Suitable chelating agents will generally have a calcium binding constant of about $10^1$ to $10^5$ to provide improved cleaning with reduced plaque and calculus formation. Chelating agents also have the ability to complex with metallic ions and thus aid in preventing their adverse effects on the stability or appearance of products. Chelation of ions, such as iron or copper, helps retard oxidative deterioration of finished products.

Examples of suitable chelating agents are sodium or potassium gluconate and citrate; citric acid/alkali metal citrate combination; disodium tartrate; dipotassium tartrate; sodium potassium tartrate; sodium hydrogen tartrate; potassium hydrogen tartrate; sodium, potassium or ammonium polyphosphates and mixtures thereof. The chelating agent may be used from about 0.1% to about 2.5%, preferably from about 0.5% to about 2.5% and more preferably from about 1.0% to about 2.5%.

Still other chelating agents suitable for use in the present invention are the anionic polymeric polycarboxylates. Such materials are well known in the art, being employed in the form of their free acids or partially or preferably fully neutralized water soluble alkali metal (e.g. potassium and preferably sodium) or ammonium salts. Examples are 1:4 to 4:1 copolymers of maleic anhydride or acid with another polymerizable ethylenically unsaturated monomer, preferably methyl vinyl ether (methoxyethylene) having a molecular weight (M.W.) of about 30,000 to about 1,000,000. These copolymers are available for example as Gantrez AN 139 (M.W. 500,000), AN 119 (M.W. 250,000) and S-97 Pharmaceutical Grade (M.W. 70,000), of GAF Chemicals Corporation.

Other operative polymeric polycarboxylates include the 1:1 copolymers of maleic anhydride with ethyl acrylate, hydroxyethyl methacrylate, N-vinyl-2-pyrrolidone, or ethylene, the latter being available for example as Monsanto EMA No. 1103, M.W. 10,000 and EMA Grade 61, and 1:1 copolymers of acrylic acid with methyl or hydroxyethyl methacrylate, methyl or ethyl acrylate, isobutyl vinyl ether or N-vinyl-2-pyrrolidone. Additional operative polymeric polycarboxylates are disclosed in U.S. Pat. No. 4,138,477 to Gaffar and U.S. Pat. No. 4,183,914 to Gaffar et al. and include copolymers of maleic anhydride with styrene, isobutylene or ethyl vinyl ether; poly acrylic, polyitaconic and polymaleic acids; and sulfoacrylic oligomers of MW as low as 1,000 available as Uniroyal ND-2.

Surfactants

The present compositions will typically also comprise surfactants, also commonly referred to as sudsing agents. Suitable surfactants are those which are reasonably stable and foam throughout a wide pH range. The surfactant may be anionic, nonionic, amphoteric, zwitterionic, cationic, or mixtures thereof. Preferred surfactants or surfactant mixtures are those that are compatible with other components particularly actives and functional excipients whose activities may be compromised. For example, anionic surfactants, such as sodium alkyl sulfate and amphoteric surfactants, such as cocoamidopropyl betaine may be preferred for use when anionic agents such as polyphosphates and organophosphates are included in the compositions.

Anionic surfactants useful herein include the water-soluble salts of alkyl sulfates having from 8 to 20 carbon atoms in the alkyl radical (e.g., sodium alkyl sulfate) and the water-soluble salts of sulfonated monoglycerides of fatty acids having from 8 to 20 carbon atoms. Sodium lauryl sulfate (SLS) and sodium coconut monoglyceride sulfonates are examples of anionic surfactants of this type. Other suitable anionic surfactants are sarcosinates, such as sodium lauroyl sarcosinate, taurates, sodium lauryl sulfoacetate, sodium lauroyl isethionate, sodium laureth carboxylate, and sodium dodecyl benzenesulfonate. Mixtures of anionic surfactants can also be employed. Many suitable anionic surfactants are disclosed by Agricola et al., U.S. Pat. No. 3,959,458. The present composition typically comprises an anionic surfactant at a level of from about 0.025% to about 9%, from about 0.05% to about 5% or from about 0.1% to about 1%.

Another suitable surfactant is one selected from the group consisting of sarcosinate surfactants, isethionate surfactants and taurate surfactants. Preferred for use herein are alkali metal or ammonium salts of these surfactants, such as the sodium and potassium salts of the following: lauroyl sarcosinate, myristoyl sarcosinate, palmitoyl sarcosinate, stearoyl sarcosinate and oleoyl sarcosinate.

Zwitterionic or amphoteric surfactants useful in the present invention include derivatives of aliphatic quaternary ammonium, phosphonium, and sulfonium compounds, in which the aliphatic radicals can be straight chain or branched, and wherein one of the aliphatic substituents contains from about 8 to 18 carbon atoms and one contains an anionic water-solubilizing group, e.g., carboxy, sulfonate, sulfate, phosphate or phosphonate. Suitable betaine surfactants are disclosed in U.S. Pat. No. 5,180,577 to Polefka et al. Typical alkyl dimethyl betaines include decyl betaine or 2-(N-decyl-N,N-dimethylammonio)acetate, coco betaine or 2-(N-coco-N,N-dimethyl ammonio)acetate, myristyl betaine, palmityl betaine, lauryl betaine, cetyl betaine, cetyl betaine, stearyl betaine, etc. The amidobetaines are exemplified by cocoamidoethyl betaine, cocamidopropyl betaine (CAPB), and lauramidopropyl betaine.

Cationic surfactants useful in the present invention include derivatives of quaternary ammonium compounds having one long alkyl chain containing from about 8 to 18 carbon atoms such as lauryl trimethylammonium chloride; cetyl pyridinium chloride; cetyl trimethylammonium bromide; coconut alkyltrimethylammonium nitrite; cetyl pyridinium fluoride; etc. Preferred compounds are the quaternary ammonium fluorides having detergent properties described in U.S. Pat. No. 3,535,421 to Briner et al. Certain cationic surfactants can also act as antimicrobials in the compositions disclosed herein.

Useful nonionic surfactants include compounds produced by the condensation of alkylene oxide groups (hydrophilic in nature) with an organic hydrophobic compound which may be aliphatic or alkylaromatic in nature. Examples of suitable nonionic surfactants include the Pluronics, polyethylene oxide condensates of alkyl phenols, products derived from the condensation of ethylene oxide with the reaction product of propylene oxide and ethylene diamine, ethylene oxide condensates of aliphatic alcohols, long chain tertiary amine oxides, long chain tertiary phosphine oxides, long chain dialkyl sulfoxides and mixtures of such materials.

Abrasives

Dental abrasives useful in the compositions of the subject invention include many different materials. The material selected must be one which is compatible within the composition of interest and does not excessively abrade dentin. Suitable abrasives include, for example, silicas including gels and precipitates, insoluble sodium polymetaphosphate, hydrated alumina, calcium carbonate, dicalcium orthophosphate dihydrate, calcium pyrophosphate, tricalcium phosphate, calcium polymetaphosphate, and resinous abrasive materials such as particulate condensation products of urea and formaldehyde.

Another class of abrasives for use in the present compositions is the particulate thermo-setting polymerized resins as described in U.S. Pat. No. 3,070,510 issued to Cooley & Grabenstetter. Suitable resins include, for example, melamines, phenolics, ureas, melamine-ureas, melamine-formaldehydes, urea-formaldehyde, melamine-urea-formaldehydes, cross-linked epoxides, and cross-linked polyesters.

Silica dental abrasives of various types are preferred because of their unique benefits of exceptional dental cleaning and polishing performance without unduly abrading tooth enamel or dentine. The silica abrasive polishing materials herein, as well as other abrasives, generally have an average particle size ranging between about 0.1 to about 30 microns, and preferably from about 5 to about 15 microns. The abrasive can be precipitated silica or silica gels such as the silica xerogels described in Pader et al., U.S. Pat. No. 3,538,230 and DiGiulio, U.S. Pat. No. 3,862,307. Examples include the silica xerogels marketed under the trade name "Syloid" by the W.R. Grace & Company, and precipitated silica materials such as those marketed by the J. M. Huber Corporation under the trade name, Zeodent®, particularly the silicas carrying the designation Zeodent® 119, Zeodent® 118, Zeodent® 109 and Zeodent® 129. The types of silica dental abrasives useful in the toothpastes of the present invention are described in more detail in Wason, U.S. Pat. No. 4,340,583; and in commonly-assigned U.S. Pat. Nos. 5,603,920; 5,589,160; 5,658, 553; 5,651,958; and 6,740,311. The silica abrasives described therein include various grades of silica such as standard or base silica and high-cleaning or high-polishing silica.

Mixtures of abrasives can be used such as mixtures of the various grades of Zeodent® silica abrasives listed above. The total amount of abrasive in dentifrice compositions of the subject invention typically range from about 6% to about 70% by weight; toothpastes preferably contain from about 10% to about 50% of abrasives. Dental solution, mouth spray, mouthwash and non-abrasive gel compositions of the subject invention typically contain little or no abrasive.

Miscellaneous Carrier Materials

Water employed in the preparation of commercially suitable oral compositions should preferably be of low ion content and free of organic impurities. Water may comprise up to about 99% by weight of the aqueous compositions herein. These amounts of water include the free water which is added plus that which is introduced with other materials, such as with sorbitol.

The present invention may also include an alkali metal bicarbonate salt, which may serve a number of functions including abrasive, deodorant, buffering and adjusting pH. Alkali metal bicarbonate salts are soluble in water and unless stabilized, tend to release carbon dioxide in an aqueous system. Sodium bicarbonate, also known as baking soda, is a commonly used bicarbonate salt. The present composition may contain from about 0.5% to about 30% by weight of an alkali metal bicarbonate salt.

The present compositions in the form of toothpastes, dentifrices and gels typically will contain some thickening material or binder to provide a desirable consistency. Preferred thickening agents include carboxyvinyl polymers, carrageenan, hydroxyethyl cellulose, and water soluble salts of cellulose ethers such as sodium carboxymethylcellulose and sodium hydroxyethyl cellulose. Natural gums such as gum karaya, xanthan gum, gum arabic, and gum tragacanth can also be used. Colloidal magnesium aluminum silicate or finely divided silica can be used as part of the thickening agent to further improve texture. Thickening agents are typically used in an amount from about 0.1% to about 15%, by weight.

Another optional component of the present compositions is a humectant, which serves to keep toothpaste compositions from hardening upon exposure to air. Certain humectants can also impart desirable sweetness of flavor to toothpaste compositions. Suitable humectants for use in the invention include glycerin, sorbitol, polyethylene glycol, propylene glycol, and other edible polyhydric alcohols. The humectant generally comprises from about 0% to 70%, preferably from about 15% to 55%, by weight of the composition.

The pH of the present compositions may be adjusted through the use of buffering agents. Buffering agents, as used herein, refer to agents that can be used to adjust the pH of aqueous compositions such as mouthrinses and dental solutions preferably to a range of about pH 4.0 to about pH 8.0. Buffering agents include sodium bicarbonate, monosodium phosphate, trisodium phosphate, sodium hydroxide, sodium carbonate, sodium acid pyrophosphate, citric acid, and sodium citrate and are typically included at a level of from about 0.5% to about 10% by weight.

Poloxamers may be employed in the present compositions. A poloxamer is classified as a nonionic surfactant and may also function as an emulsifying agent, binder, stabilizer, and other related functions. Poloxamers are difunctional blockpolymers terminating in primary hydroxyl groups with molecular weights ranging from 1,000 to above 15,000. Poloxamers are sold under the tradename of Pluronics and Pluraflo by BASF including Poloxamer 407 and Pluraflo L4370.

Other emulsifying agents that may be used include polymeric emulsifiers such as the Pemulen® series available from B.F. Goodrich, and which are predominantly high molecular weight polyacrylic acid polymers useful as emulsifiers for hydrophobic substances.

Titanium dioxide may also be added to the present compositions as coloring or opacifying agent typically at a level of from about 0.25% to about 5% by weight.

Other optional agents that may be used in the present compositions include dimethicone copolyols selected from alkyl- and alkoxy-dimethicone copolyols, such as C12 to C20 alkyl dimethicone copolyols and mixtures thereof, as aid in providing positive tooth feel benefits. Highly preferred is cetyl dimethicone copolyol marketed under the trade name Abil EM90. The dimethicone copolyol is generally present from about 0.01% to about 25%, preferably from about 0.1% to about 5 by weight.

Method of Use

A method of use or treatment herein comprises contacting a subject's dental enamel surfaces and mucosa in the mouth with the oral compositions according to the present invention. The method may be by brushing with a dentifrice or rinsing with a dentifrice slurry or mouthrinse. Other methods include contacting the topical oral gel, denture product, mouthspray, or other form with the subject's teeth and oral mucosa. The subject may be any person or animal whose oral cavity is contacted with the oral composition. By animal is meant to include household pets or other domestic animals, or animals kept in captivity.

For example, a method of treatment may include brushing a dog's teeth with a dentifrice composition. Another example would include rinsing a cat's mouth with an oral composition for a sufficient amount of time to see a benefit. Pet care products such as chews and toys may be formulated to contain the present oral compositions. The composition may be incorporated into a relatively supple but strong and durable material such as rawhide, ropes made from natural or synthetic fibers, and polymeric articles made from nylon, polyester or thermoplastic polyurethane. As the animal chews, licks or gnaws the product, the incorporated active elements are released into the animal's oral cavity into a salivary medium, comparable to an effective brushing or rinsing.

In one embodiment of the present invention, the method of use involves a regimen that comprises brushing with a dentifrice containing the coolant(s) followed by rinsing with a rinse containing a potentiating agent for the coolant(s). Or the dentifrice may contain the potentiating agent and the rinse will contain the coolant(s). The regimen approach is advantageous for example, when the potentiating agent such as a calcium ion source may present stability problems with components of either the dentifrice or rinse or when there is a desire to delay the onset of the enhancing effect. In addition rinsing would ensure distribution of coolant and potentiating agent throughout the mouth resulting in a whole mouth feeling of refreshing cool sensation. In another embodiment, the regimen comprises brushing or rinsing with a product containing a calcium ion source, followed by chewing gum or sucking on a lozenge containing coolant(s) to deliver long lasting cool sensation. Alternatively, the coolant(s) and potentiating agent may be present in all products used in the regimens.

EXAMPLES

The following examples further describe and demonstrate embodiments within the scope of the present invention. These examples are given solely for the purpose of illustration and are not to be construed as limitations of the present invention as many variations thereof are possible without departing from the spirit and scope.

Example I

Preparation of N-[4-(cyanomethyl)phenyl]-(1R,2S, 5R)-2-isopropyl-5-methylcyclohexanecarboxamide A. Preparation of (1R,2S,5R)-2-isopropyl-5-methyl-cyclohexanecarboxamide A 250 mL flask was purged with nitrogen, left under a nitrogen atmosphere, and charged with 13.0 g (0.0641 mol) of (1R,2S,5R)-2-isopropyl-5-methylcyclohexanecarbonyl chloride. While stirring 130 mL of 29% ammonium hydroxide solution was added to the flask. A white precipitate quickly formed, and after stirring overnight the fine white slurry was suction filtered. The filter cake was washed with water (3×50 mL) then dried in a vacuum oven (RT, 5 mm Hg, 3 days) to provide (1R,2S,5R)-2-isopropyl-5-methylcyclohexanecarboxamide as a white solid with the following spectroscopic properties.

$^1$H NMR (500 MHz, CDCl$_3$): δ 0.78 (d, 3H), 0.88 (d, 3H), 0.91 (d, 3H), 1.00 (m, 2H), 1.20 (m, 1H), 1.38 (m, 1H), 1.50 (m, 1H), 1.63-1.90 (m, 4H), 2.08 (td, 1H), 5.45 (br s, 2H).
$^{13}$C NMR (125 MHz, CDCl$_3$): δ 16.26, 21.65, 22.57, 23.98, 28.84, 32.52, 34.80, 39.73, 44.65, 49.30, 178.82.
MS (Ionspray): m/e 184 (MH$^+$, 100%)

B. Coupling of (1R,2S,5R)-2-isopropyl-5-methylcyclohexanecarboxamide with 4-(cyanomethyl)phenyl iodide A 250 mL 3-neck flask was fitted with a condenser and a nitrogen inlet was charged with 10.00 g (0.0546 mol) of (1R,2S,5R)-2-isopropyl-5-methylcyclohexanecarboxamide, 0.522 g (0.0027 mol) copper (I) iodide, 13.26 g (0.0546 mol) of 4-(cyanomethyl)phenyl iodide, 23.18 g (0.109 mol) of potassium phosphate. The system was purged with nitrogen and a magnetic stir bar was added. After the addition of 170 mL of toluene, 3.42 g (0.190 mol) of water and 0.964 g (0.0109 mol) of N,N'-dimethylethylene diamine, the mixture was heated to 100° C. and stirred for 21 h under nitrogen. The crude reaction mixture was filtered through 50 g of silica gel (wet with 1:1 ethyl acetate/methylene chloride), and the bed was rinsed three times with 1:1 ethyl acetate/methylene chloride (150+75+75 mL). Concentration of the mixture in vacuo provided N-[4-(cyanomethyl)phenyl]-(1R,2S,5R)-2-isopropyl-5-methylcyclohexanecarboxamide as a thick oil oil which was further purified by flash chromatography on silica gel eluting with mixtures of ethyl acetate and hexanes. The product has the following properties with the structure confirmed by obtaining an X-ray crystal structure of a sample crystallized from hexane/ethyl acetate.

$^1$H NMR (500 MHz, CDCl$_3$): δ 0.82 (d, 3H), 0.89 (d, 3H), 0.93 (d, 3H), 0.95-1.06 (m, 2H), 1.35 (m, 1H), 1.38 (m, 1H), 1.63 (t, 1H), 1.71-1.83 (m, 3H), 1.91 (d, 1H), 2.20 (td, 1H), 3.72 (s, 2H), 7.23 (d, 2H), 7.51 (br s, 1H), 7.56 (d, 2H).

$^{13}$C NMR (125 MHz, CDCl$_3$): δ 16.54, 21.64, 22.55, 23.33, 24.10, 29.09, 32.52, 34.71, 39.63, 44.76, 50.90, 118.24, 120.68, 125.48, 128.74, 138.22, 174.86.

MS (Ionspray): m/e 299 (MH$^+$, 100%)

Mp: 146.0-149.5° C.

$[\alpha]^{27.5}_D$ –42.9° (0.0103 g/mL, CHCl$_3$)

Crystal Data and Structure Refinement:

| | |
|---|---|
| Empirical formula | C19H26N2O |
| Formula weight | 298.42 |
| Temperature | 571(2) K |
| Wavelength | 1.54178 A |
| Crystal system | Orthorhombic |
| Space group | P2$_1$2$_1$2$_1$ |
| Unit cell dimensions | a = 5.21430(10) A    alpha = 90 deg. |
| | b = 17.3974(5) A     beta = 90 deg. |
| | c = 19.4797(6) A     gamma = 90 deg. |
| Volume, Z | 1767.11(8) A^3, 4 |
| Density (calculated) | 1.122 Mg/m^3 |
| Absorption coefficient | 0.538 mm^-1 |
| F(000) | 648 |
| Crystal size | 0.3 × 0.2 × 0.1 mm |
| Theta range for data collection | 3.41 to 71.28 deg. |
| Limiting indices | −6 <= h <= 5, −20 <= k <= 21, −23 <= l <= 23 |
| Reflections collected | 13300 |
| Independent reflections | 3316 [R(int) = 0.0566] |
| Refinement method | Full-matrix least-squares on F^2 |
| Data/restraints/parameters | 3315/0/199 |
| Goodness-of-fit on F^2 | 1.040 |
| Final R indices [I > 2sigma(I)] | R1 = 0.1001, wR2 = 0.2688 |
| R indices (all data) | R1 = 0.1288, wR2 = 0.3065 |
| Absolute structure parameter | 0.2(8) |
| Largest diff. peak and hole | 0.854 and −0.424 e · A^−3 |

Example II

Preparation of (1S,2S,5R)-2-isopropyl-5-methylcyclohexanecarboxamide and N-[4-(cyanomethyl)phenyl]-(1S,2S,5R)-2-isopropyl-5-methylcyclohexanecarboxamide A. Preparation of (1R,2S,5R)-menthyl tosylate A solution of 50.10 g (0.321 mol) of (1R,2S,5R)-(−)-menthol in 300 mL of pyridine in a 1 L Erlenmeyer flask was cooled to 0° C. in an ice bath, and 91.0 g (0.477 mol) of p-toluenesulfonyl chloride (TsCl) was added with stirring. The solution was kept in the ice bath between 0-10° C. for 2 h then sealed and stored in a 5° C. refrigerator for 23 h. The reaction mixture was poured into 5 L of an ice/water mixture with stirring leading to a precipitate which was suction filtered after 30 min. The white precipitate was rinsed on the funnel with 3×500 mL of water, then dried in a vacuum oven for 3 days (RT, 5 mm Hg) to provide the desired (1R,2S,5R)-menthyl tosylate for use in the preparation of the carbonitrile below (step B) having opposite stereochemistry at the C-1 position.

$^1$H NMR (500 MHz, CDCl$_3$): δ 0.55 (d, 3H), 0.82 (d, 3H), 0.90 (d, 3H), 0.98 (m, 1H), 1.19 (m, 1H), 1.40 (m, 2H), 1.62 (m, 2H), 1.89 (m, 1H), 2.16 (d, 1H), 2.43 (s, 3H), 4.40 (m, 1H), 7.34 (d, 2H), 7.80 (d, 2H).

$^{13}$C NMR (125 MHz, CDCl$_3$): δ 15.46, 21.09, 21.87, 22.11, 23.17, 25.70, 31.90, 33.99, 42.19, 47.80, 83.92, 127.92, 129.91, 134.98, 144.56.

B. Preparation of (1S,2S,5R)-2-isopropyl-5-methylcyclohexanecarbonitrile

To a solution of 6.33 g (20.4 mmol) of (1R,2S,5R)-menthyl tosylate in 100 mL of dimethyl sulfoxide at room temperature was added 2.00 g (40.8 mmol) of sodium cyanide. The mixture was heated to 90° C. under a nitrogen atmosphere for 5 h. After cooling to room temperature the mixture was diluted with 250 mL of water and extracted with 3×250 mL of ethyl acetate. The combined organic layers were extracted with 100 mL of water, dried over magnesium sulfate, and concentrated in vacuo to provide (1S,2S,5R)-2-isopropyl-5-methylcyclohexanecarbonitrile as a light yellow liquid.

$^1$H NMR (500 MHz, CDCl$_3$): δ 0.80-1.00 (m, 2H), 0.92 (d, 3H), 0.96 (d, 6H), 1.11.17 (t, 1H), 1.29 (q, 1H), 1.60 (m, 1H), 1.75 (m, 1H), 1.80 (2, 1H), 1.92 (d, 1H), 2.00 (d, 1H), 3.08 (br s, 1H).

$^{13}$C NMR (125 MHz, CDCl$_3$): δ 20.82, 20.95, 22.01, 27.15, 28.70, 31.34, 31.46, 34.72, 37.56, 45.82, 121.27.

C. Preparation of (1S,2S,5R)-2-isopropyl-5-methylcyclohexanecarboxamide

A solution of 0.105 g (0.634 mmol) of (1S,2S,5R)-2-isopropyl-5-methylcyclohexanecarbonitrile in 4.9 mL of dimethyl sulfoxide was placed in a 10 mL flask with a magnetic stir bar. After adding 0.60 mL of 35% hydrogen peroxide and 0.097 g (1.2 mmol) of 50% sodium hydroxide solutions the flask was capped and stirred at room temperature for 20 h. The reaction mixture was diluted with 10 mL of water, extracted twice with 10 mL of methylene chloride. The combined methylene chloride layers were back extracted with 3×20 mL of water, dried over magnesium sulfate, and concentrated in vacuo to provide an off-white solid that was further purified by column chromatography (silica gel, 75:25 hexane:ethyl acetate) to provide (1S,2S,5R)-2-isopropyl-5-methylcyclohexanecarboxamide.

$^1$H NMR (500 MHz, CDCl$_3$): δ 0.82 (d, 3H), 0.91 (d, 3H), 0.94 (d, 3H), 0.94-1.05 (m, 2H), 1.19 (td, 1H), 1.68 (m, 2H), 1.75-1.90 (m, 4H), 2.66 (br s, 1H), 5.50 (br s, 2H).

$^{13}$C NMR (125 MHz, CDCl$_3$): δ 21.65, 21.83, 22.73, 25.74, 27.40, 30.62, 35.54, 39.50, 42.80, 46.74, 178.04.

MS (Ionspray): m/e 184 (MH$^+$, 100%)

D. Preparation of N-[4-(cyanomethyl)phenyl]-(1S,2S,5R)-2-isopropyl-5-methylcyclohexanecarboxamide N-[4-(cyanomethyl)phenyl]-(1S,2S,5R)-2-isopropyl-5-methylcyclohexanecarboxamide was prepared as described above for the preparation of the N-[4-(cyanomethyl)phenyl]-(1R,2S,5R)-2-isopropyl-5-methylcyclohexanecarboxamide isomer, i.e., by coupling the (1S,2S,5R)-2-isopropyl-5-methylcyclohexanecarboxamide prepared in steps A to C above with 4-(cyanomethyl)phenyl iodide. The (1S,2S,5R)-material (neoisomer) has the following properties with structure confirmed by obtaining an X-ray crystal structure of a sample crystallized from hexane/ethyl acetate.

$^1$H NMR (500 MHz, CDCl$_3$): δ 0.80 (d, 3H), 0.90 (d, 3H), 0.93 (d, 3H), 0.93-1.25 (m, 2H), 1.21 (m, 1H), 1.68 (m, 2H), 1.75-1.95 (m, 4H), 2.68 (m, 1H), 5.50 (br s, 2H).

$^{13}$C NMR (125 MHz, CDCl$_3$): δ 21.65, 21.83, 22.73, 25.74, 27.40, 30.62, 35.54, 39.50, 42.80, 46.74, 178.04.

MS (Ionspray): m/e 299 (MH$^+$, 100%)

Mp: 167.0-169.0° C.

$[\alpha]^{27.5}{}_D$ +9.7° (0.0100 g/mL, CHCl$_3$)

Crystal Data and Structure Refinement:

| | |
|---|---|
| Empirical formula | C19H26N2O |
| Formula weight | 298.42 |
| Temperature | 571(2) K |
| Wavelength | 1.54178 A |
| Crystal system | Orthorhombic |
| Space group | P2$_1$2$_1$2$_1$ |
| Unit cell dimensions | a = 9.7487(3) A    alpha = 90 deg. |
| | b = 11.0154(3) A   beta = 90 deg. |
| | c = 16.0495(4) A   gamma = 90 deg. |
| Volume, Z | 1723.49(8) A^3, 4 |
| Density (calculated) | 1.150 Mg/m^3 |
| Absorption coefficient | 0.551 mm^−1 |
| F(000) | 648 |
| Crystal size | 0.3 × .2 × 1 mm |
| Theta range for data collection | 4.87 to 71.24 deg. |
| Limiting indices | −11 <= h <= 9, −13 <= k <= 12, −19 <= l <= 19 |
| Reflections collected | 13352 |
| Independent reflections | 3242 [R(int) = 0.0620] |
| Refinement method | Full-matrix least-squares on F^2 |
| Data/restraints/parameters | 3241/0/199 |
| Goodness-of-fit on F^2 | 1.004 |
| Final R indices [I > 2sigma(I)] | R1 = 0.0441, wR2 = 0.0997 |
| R indices (all data) | R1 = 0.0682, wR2 = 0.1136 |
| Absolute structure parameter | −0.2(4) |
| Largest diff. peak and hole | 0.118 and −0.150 e · A^−3 |

Example III

Dentifrice Compositions

Dentifrice compositions (A-C) comprising the G-180 and neoisomer coolants made in Examples I and II respectively, were prepared using conventional methods. Ingredients are shown in weight %. Results of sensory evaluation of the compositions using a three-judge panel are shown below. Panelists brushed with each dentifrice and then rated the sensation after 10 minutes using a 5-point scale with 5 having the highest intensity. The duration of the overall sensation which included cooling as well as some peppery/irritation/burning in some cases was recorded up to when no more cooling/sensation occurred.

| | Dentifrice | | |
|---|---|---|---|
| Ingredients | A Wt. % | B Wt. % | C Wt. % |
| Sorbitol | 52.645 | 52.645 | 52.645 |
| Sodium Hydroxide | 2.3 | 2.3 | 2.3 |
| Silica 119 | 15.0 | 15.0 | 15.0 |
| Xanthan Gum | 0.7 | 0.7 | 0.7 |
| Sodium Carboxymethylcellulose | 0.2 | 0.2 | 0.2 |
| Sodium Acid Pyrophosphate | 4.4 | 4.4 | 4.4 |
| DI Water | 10.0 | 10.0 | 10.0 |
| Carbomer 956 | 0.4 | 0.4 | 0.4 |
| Sodium Lauryl Sulfate (28% Solution) | 5.0 | 5.0 | 5.0 |
| Sodium Saccharin | 0.54 | 0.54 | 0.54 |
| G-180 (Example I) | 0.015 | — | 0.0075 |
| Neo-G-180 (Example II) | — | 0.015 | 0.0075 |
| Rectified Peppermint Oil | 1.0 | 1.0 | 1.0 |
| Silica | 7.8 | 7.8 | 7.8 |
| Sensory Evaluation | | | |
| Sensation Score (After 10 min) | 3.7 | 2.9 | 4.6 |
| Sensation Duration (minutes) | 46.0 | 37.0 | 78.7 |

Example IV

Coolant Activity of Neoisomers

The neo-coolants synthesized according to the routes outlined herein were tested to rate their cooling power compared with the corresponding l-isomers (commercially available samples) using the following protocol. Control and test coolants were formulated into a dentifrice at various levels according to the following formula.

| Dentifrice Formulation With Coolant | Level |
|---|---|
| Silica, Dental Type, NF (Zeodent 119) | 5.00% |
| Titanium Dioxide for Dentifrice USP | 0.53% |
| Carboxymethylcellulose Sodium, USP (7M8SF) | 0.75% |
| Tribasic Sodium Phosphate Dodecahydrate | 1.10% |
| Sorbitol Solution, USP (LRS) | 60.88% |
| Carbomer 956 | 0.30% |
| Sodium Phosphate Monobasic Monohydrate, USP | 0.42% |
| Silica, Dental Type NF Zeodent 119 | 10.00% |
| Sodium Lauryl Sulfate 28% Solution | 4.00% |
| Spearmint Flavor | 1.00% |
| Coolant | variable |
| Purified Water, USP | QS |

Panelists (n=9) were instructed to brush for 30 seconds with a control dentifrice (containing a mixture of coolants 1500 ppm l-WS-3, 3000 ppm Menthol, 3000 ppm MGA and 1000 ppm WS-23), expectorate, and assign the control dentifrice a cooling rating of 60 on a 1-90 scale. The panelists were then given the test dentifrices in random order and instructed to brush and rate each sample relative to the control over a 60-minute period. Cooling ratings relative to control are summarized below.

| | Cooling Rating Relative to Control | | | | |
|---|---|---|---|---|---|
| Coolants | 0 min | 15 min | 30 min | 45 min | 60 min |
| 1500 ppm l-WS-3 | 53.5 | 36.5 | 27.0 | 20.5 | 15.5 |
| 1500 ppm Neo-WS-3 | 43.3 | 33.9 | 23.3 | 16.7 | 13.3 |
| 750 ppm Neo-WS-3 + 750 ppm l-WS-3 | 51.5 | 33.0 | 21.5 | 14.0 | 9.0 |
| 1500 ppm l-WS-5 | 53.9 | 40.0 | 26.7 | 17.8 | 13.3 |
| 1500 ppm NeoWS-5 | 61.9 | 39.3 | 29.3 | 21.4 | 15.7 |
| 750 ppm Neo-WS-5 + 750 ppm l-WS-5 | 57.0 | 44.0 | 29.0 | 21.5 | 14.0 |
| 500 ppm l-Menthyl lactate (2S) | 50.0 | 38.0 | 26.5 | 18.5 | 13.5 |
| 500 ppm Neo-Menthyl lactate (2S) | 62.2 | 43.9 | 33.9 | 27.5 | 16.7 |

-continued

| Coolants | Cooling Rating Relative to Control | | | | |
|---|---|---|---|---|---|
| | 0 min | 15 min | 30 min | 45 min | 60 min |
| 1950 ppm Neo-Menthyl lactate (~2:1 S:R) | 50.6 | 42.8 | 30.6 | 22.2 | 16.7 |
| 1000 ppm Neo-Menthyl pyruvate | 57.8 | 45.0 | 30.6 | 21.1 | 16.1 |
| 335 ppm Neo-Menthyl lactate acetate (2S) | 64.4 | 46.3 | 33.1 | 26.3 | 21.3 |

The neoisomers of WS-5 and menthyl lactate showed higher cooling potency over the l-isomers. Where the neoisomer did not show higher cooling potency such as with WS-3, blending of the two isomers may still be advantageous in providing a better in-use experience, such as was demonstrated with the G-180 and neo-G-180 blend, wherein the negative sensory effects from using G-180 alone was modulated by the neoisomer. This is believed to result from having two different binding patterns at the same coolant receptor site. The neo-derivatives of menthyl lactate showed surprising cooling power. In particular, neo-menthyl lactate (2S) and neo-menthyl lactate acetate [(1S,2S,5R)-2-isopropyl-5-methylcyclohexyl-2(S)-acetoxypropanoate] provided very strong initial cooling as well as over the 60 minute time period, compared to 1-menthyl lactate. The other menthyl lactate derivatives exhibited a similar trend.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm".

All documents cited in the Detailed Description of the Invention are, in relevant part, incorporated herein by reference; the citation of any document is not to be construed as an admission that it is prior art with respect to the present invention. To the extent that any meaning or definition of a term in this written document conflicts with any meaning or definition of the term in a document incorporated by reference, the meaning or definition assigned to the term in this written document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A process for preparing N-substituted menthanecarboxamide of general formula

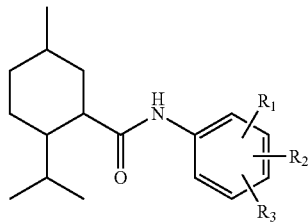

comprising a coupling reaction in the presence of a copper catalyst between a primary menthane carboxamide and an aryl halide of the general formula

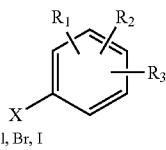

X = Cl, Br, I wherein $R_1$, $R_2$ and $R_3$ may be the same or different and may each be hydrogen or one of $R_1$, $R_2$ and $R_3$ may be a group selected from halogen, OH, hydroxy-C1-C4-alkyl, C1-C4-alkoxy, $NO_2$, CN, cyano-C1-C4-alkyl, acetyl, $SO_2NH_2$, CHO, $CO_2H$ and C1-C4 alkyl carboxylate; two of $R_1$, $R_2$ and $R_3$ may be H or C1-C4 alkyl and X is Cl, Br, I or mixtures thereof.

2. The process of claim 1 wherein the reaction is conducted in the presence of potassium phosphate and the copper catalyst is a copper halide.

3. The process of claim 2 wherein the copper halide is copper (I) iodide.

4. The process of claim 1 wherein the primary menthane carboxamide is prepared by reacting a menthane acid chloride with ammonia under aqueous conditions.

5. The process of claim 1 wherein the menthane carboxamide is prepared by hydrolysis of a corresponding menthane nitrile.

6. The process of claim 1 wherein the stereochemistry of the starting menthane carboxamide is maintained through the coupling reaction with aryl halide to produce the N-substituted menthane carboxamide.

7. The process of claim 6 wherein (1S,2S,5R)-menthane carboxamide is reacted with aryl halide to produce neoisomers having 1S,2S,5R configuration of N-aryl substituted menthane carboxamide.

* * * * *